(12) United States Patent
Soukup et al.

(10) Patent No.: US 11,369,804 B2
(45) Date of Patent: Jun. 28, 2022

(54) PARTICLE ARC TREATMENT PLANNING

(71) Applicant: Elekta, Inc., Atlanta, GA (US)

(72) Inventors: Martin Soukup, Ebensee (AT); Kun-Yu Tsai, Shanghai (CN)

(73) Assignee: Elekta, Inc., Atlanta, GA (US)

( * ) Notice: Subject to any disclaimer, the term of this patent is extended or adjusted under 35 U.S.C. 154(b) by 0 days.

(21) Appl. No.: 17/302,225

(22) Filed: Apr. 27, 2021

(65) Prior Publication Data
US 2022/0118282 A1    Apr. 21, 2022

Related U.S. Application Data

(60) Provisional application No. 63/093,139, filed on Oct. 16, 2020.

(51) Int. Cl.
*A61N 5/10*     (2006.01)
*G16H 20/40*    (2018.01)

(52) U.S. Cl.
CPC ......... *A61N 5/1031* (2013.01); *A61N 5/1081* (2013.01); *G16H 20/40* (2018.01)

(58) Field of Classification Search
CPC .... A61N 5/103–1084; A61N 2005/1085–1098
See application file for complete search history.

(56) References Cited

U.S. PATENT DOCUMENTS

| | | | |
|---|---|---|---|
| 6,501,828 B1 | 12/2002 | Popescu | |
| 2012/0136194 A1* | 5/2012 | Zhang | A61N 5/103 600/1 |
| 2013/0197878 A1 | 8/2013 | Fiege et al. | |
| 2013/0324784 A1 | 12/2013 | Fredriksson | |
| 2015/0011817 A1 | 1/2015 | Feng | |
| 2016/0059038 A1 | 3/2016 | Sloman | |
| 2017/0028221 A1* | 2/2017 | Kontaxis | A61N 5/1067 |
| 2018/0078784 A1 | 3/2018 | Schnarr | |
| 2020/0276456 A1 | 9/2020 | Swerdloff | |
| 2020/0384289 A1* | 12/2020 | Smith | A61N 5/1081 |
| 2021/0038914 A1* | 2/2021 | Traneus | A61N 5/1031 |

FOREIGN PATENT DOCUMENTS

| | | |
|---|---|---|
| EP | 2605828 | 4/2018 |
| EP | 3549636 | 10/2019 |

OTHER PUBLICATIONS

"International Application Serial No. PCT US2021 070470, International Search Report dated Jul. 7, 2021", 2 pages.

(Continued)

*Primary Examiner* — Thaddeus B Cox
(74) *Attorney, Agent, or Firm* — Schwegman Lundberg & Woessner, P.A.

(57) ABSTRACT

System and methods may be used for arc fluence optimization without iteration to arc sequence generation. A method may include defining a particle arc range for a radiotherapy treatment of a patient, and generating an arc sequence, including a set of parameters for delivering the radiotherapy treatment, without requiring a dose calculation. The method may include optimizing fluence of the arc sequence for the radiotherapy treatment without iterating back to arc sequence generation, and outputting the fluence optimized arc sequence for use in the radiotherapy treatment.

30 Claims, 22 Drawing Sheets

(56) References Cited

OTHER PUBLICATIONS

"International Application Serial No. PCT US2021 070470, Written Opinion dated Jul. 7, 2021", 3 pages.
"International Application Serial No. PCT US2021 070468, International Search Report dated Aug. 13, 2021", 2 pgs.
"International Application Serial No. PCT US2021 070468, Written Opinion dated Aug. 13, 2021", 3 pgs.

* cited by examiner

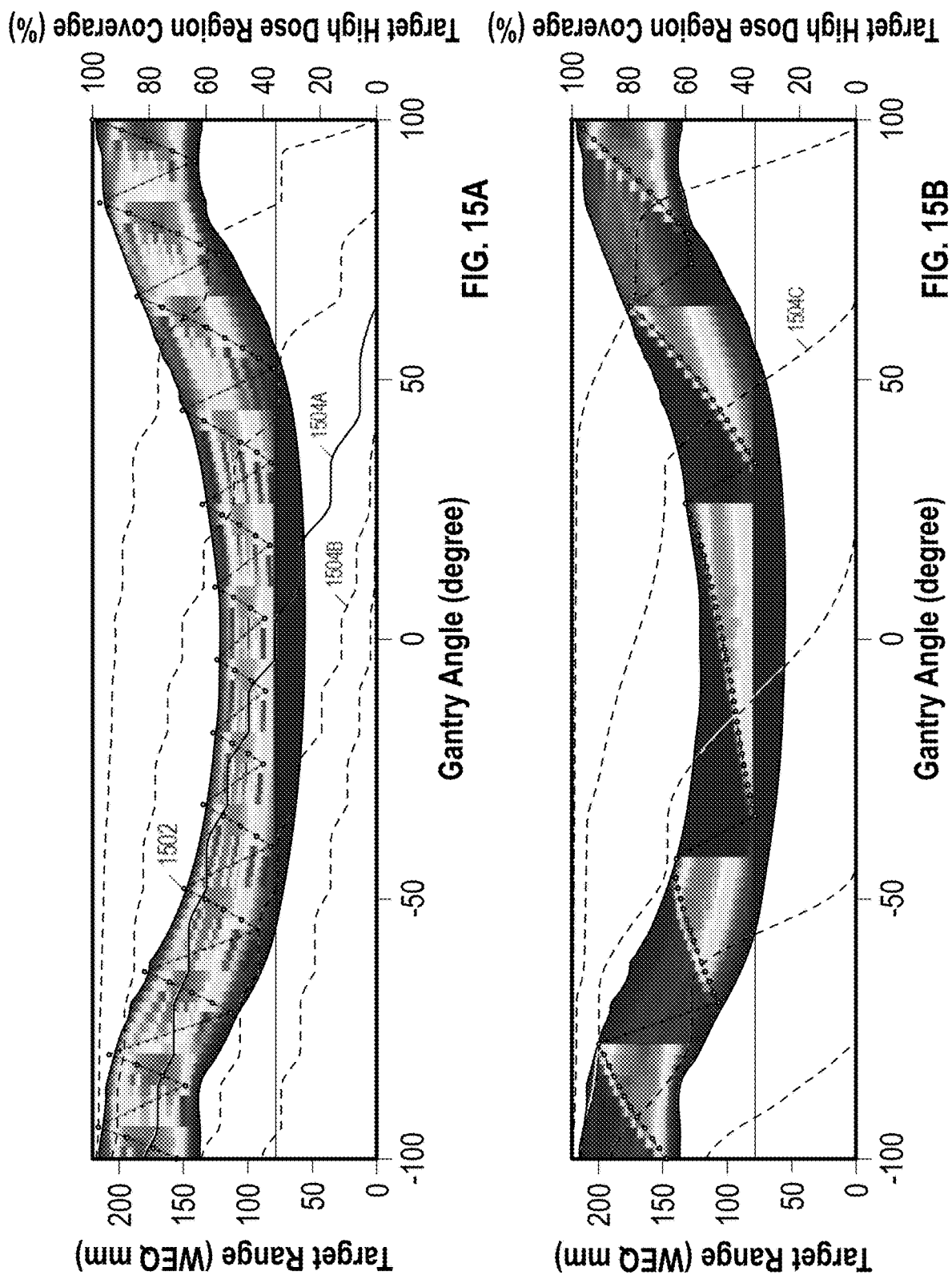

PARTICLE ARC TREATMENT PLANNING

CLAIM OF PRIORITY

This application claims the benefit of priority to U.S. Provisional Application No. 63/093,139, filed Oct. 16, 2020, tided "PARTICLE ARC TREATMENT PLANNING," which is hereby incorporated herein by reference in its entirety.

BACKGROUND

Radiation therapy or "radiotherapy" may be used to treat cancers or other ailments in mammalian (e.g., human and animal) tissue. One such radiotherapy technique is referred to as "gamma knife," by which a patient is irradiated using a number of lower-intensity gamma rays that converge with higher intensity and high precision at a targeted region (e.g., a tumor). In another example, radiotherapy is provided using a linear accelerator ("linac"), whereby a targeted region is irradiated by high-energy particles (e.g., electrons, high-energy photons, and the like). In another example, radiotherapy is provided using a heavy charged particle accelerator (e.g., protons, carbon ions, and the like). The placement and dose of the radiation beam is accurately controlled to provide a prescribed dose of radiation to the targeted region. The radiation beam is also generally controlled to reduce or minimize damage to surrounding healthy tissue, such as may be referred to as "organ(s) at risk" (OARs). Radiation may be referred to as "prescribed" because generally a physician orders a predefined dose of radiation to be delivered to a targeted region such as a tumor.

DEFINITIONS

A spot is a thin particle pencil beam defined by nominal delivery properties—e.g., energy, position, angle. Particles of a spot are delivered at a predetermined rate from a gantry angle and delivered by a nominal beam energy to a starting point and to an ending point, where starting point and ending point can be the same.

BRIEF DESCRIPTION OF THE DRAWINGS

FIGS. 13, 14A-14C, and 15A-15B illustrate arc sequencing visualizations, in accordance with an embodiment.

Figure 1:
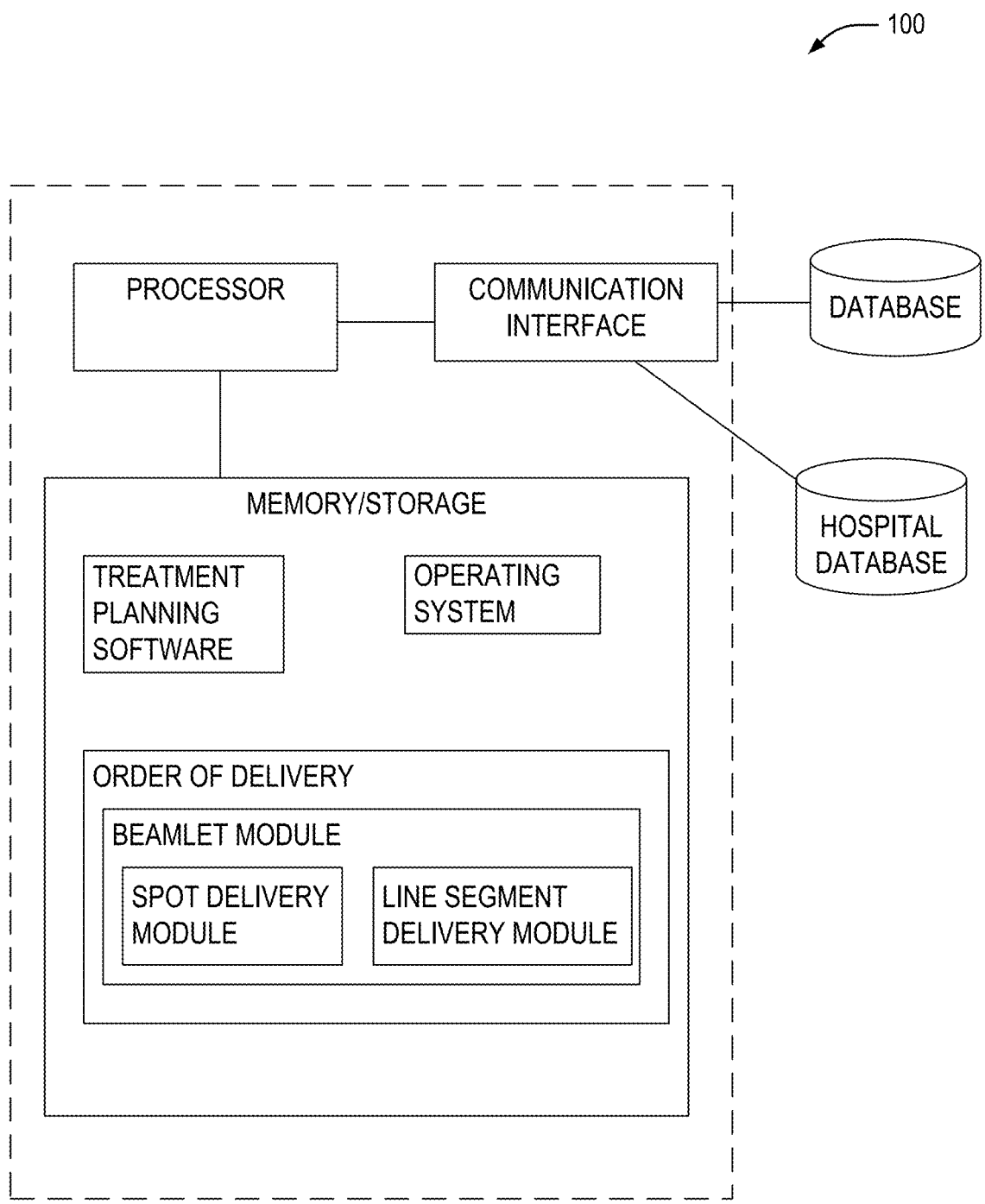
FIG. 1 illustrates generally an example of a system, such as may include a particle therapy system controller, in accordance with an embodiment.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As discussed above, radiation therapy or "radiotherapy" is used to treat cancers or other ailments in mammalian (e.g., human and animal) tissue. Generally, ionizing radiation in the form of a collimated beam is directed from an external radiation source toward a patient. Modulation of a radiation beam may be provided by one or more attenuators or collimators (e.g., a multi-leaf collimator). The intensity and shape of the radiation beam may be adjusted by collimation avoid damaging healthy tissue (e.g., OARs) adjacent to the targeted tissue by conforming the projected beam to a profile of the targeted tissue.

The treatment planning procedure may include using a three-dimensional image of the patient to identify the target region (e.g., the tumor) and such as to identify critical organs near the tumor. Creation of a treatment plan may be a time consuming process where a planner tries to comply with various treatment objectives or constraints (e.g., dose volume histogram (DVH) objectives or other constraints), such as taking into account importance (e.g., weighting) of respective constraints in order to produce a treatment plan that is clinically acceptable. This task may be a time-consuming trial-and-error process that is complicated by the various organs at risk (OARs) because as the number of OARs increases (e.g., about thirteen for a head-and-neck treatment), so does the complexity of the process. OARs distant from a tumor may be more easily spared from radiation, but OARs close to or overlapping a target tumor may be more difficult to spare from radiation exposure during treatment.

Generally, for each patient, an initial treatment plan may be generated in an "offline" manner. The treatment plan may be developed well before radiation therapy is delivered, such as using one or more medical imaging techniques. Imaging information may include, for example, images from X-rays, Computed Tomography (CT), nuclear magnetic resonance (MR), positron emission tomography (PET), single-photon emission computed tomography (SPECT), or ultrasound. A health care provider, such as a physician, may use three-dimensional imaging information indicative of the patient anatomy to identify one or more target tumors along with the organs at risk near the tumor. The health care provider may delineate the target tumor that is to receive a prescribed radiation dose using a manual technique, and the health care provider may similarly delineate nearby tissue, such as organs, at risk of damage from the radiation treatment.

Alternatively or additionally, an automated tool (e.g., ABAS® provided by Elekta AB, Sweden) may be used to assist in identifying or delineating the target tumor and organs at risk. A radiation therapy treatment plan ("treatment plan") may then be created using an optimization technique based on clinical and dosimetric objectives and constraints (e.g., the maximum, minimum, and mean doses of radiation to the tumor and critical organs).

The treatment planning procedure may include using a three-dimensional image of the patient to identify the target region (e.g., the tumor) and to identify critical organs near the tumor. Image acquisition may be performed just before initiation of delivery of a specified radiation therapy fraction. Such imaging may provide information helpful for identifying a position of a target region or for identifying motion of the target region. Such contemporaneous imaging may be referred to generically as "real-time," but in general a latency or time delay exists between an acquisition of an image and a delivery of radiation therapy.

Creation of a treatment plan may be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task may be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

The treatment plan may then be later executed by positioning the patient and delivering the prescribed radiation therapy. The radiation therapy treatment plan may include dose "fractioning," whereby a sequence of radiation therapy deliveries are provided over a predetermined period of time (e.g., 45 fractions or some other total count of fractions), such as with each therapy delivery including a specified fraction of a total prescribed dose. During treatment, the position of the patient or the position of the target region in relation to the treatment beam is important because such positioning in part determines whether the target region or healthy tissue is irradiated.

In one approach, radiation therapy may be provided by using particles, such as protons, instead of electrons. This typically may be referred to as proton therapy. One significant known advantage of proton therapy is it provides superior dose distribution with minimal exit dose compared to other forms of radiation therapy, such as x-ray therapy. There is a significant reduction of dose to organs at risk (OAR) because of the minimal exit dose. Further advantages include lower dose per treatment, which lowers the risk of side effects and may improve quality of life during and after proton therapy treatment.

One method of providing proton therapy is to use a broad proton beam, such as a spread-out Bragg peak that provides a uniform beam having multiple energies. If various energy fields are to be used to treat the patient, it may not be accomplished using a broad beam. For example, a broad beam requires an ion beam compensator per treatment field customized per patient. This means there would be one compensator required for every angle, therefore, multiple compensators would have to be used to treat a patient. For example, for at least every 4 degrees, a different compensator would have to be used. Treatment would have to be stopped and started using 90 different ion compensators to provide a 360 degree rotational proton radiation therapy. Another issue with using a broad beam is there is an undesired shape to the dose at the proximal edge of the targeted tumor.

FIG. 1 illustrates generally an example of a system 100, such as may include a particle therapy system controller, in accordance with an embodiment. The system 100 may include a database or a hospital database. The particle therapy system controller may include a processor, communication interface, or memory. The memory may include treatment planning software, an operating system, or a delivery controller. The delivery controller may include a beamlet module for determining or planning spot delivery (e.g., using a spot delivery module) or line segment delivery (e.g., using a line segment delivery module).

In an example, the spot delivery module or the beamlet module may be configured to plan size of beamlets, location of a target or spot, or the like. The beamlet module may be used to determine an order of delivery of beamlets, for example in a spiral pattern as described herein. The order of delivery module may be in communication with the treatment planning software for planning delivery of beamlets. For example, the treatment planning software may be used to determine or plan gantry angle, gantry speed, beamlet size, spiral pattern (e.g., clockwise or counterclockwise), angle range for a particular spiral pattern (e.g., every ten degrees of the gantry rotation), or the like.

The processor may implement the plan, such as by communicating, via the communication interface or otherwise, to components used to implement the plan (e.g., to control devices or components, such as those described below with reference to FIG. 3). In an example, the communication interface may be used to retrieve stored information from a database or a hospital database (e.g., patient information, past procedure information for the patient or other patients, procedure instructions, information about particular devices or components, or the like).

Figure 2:
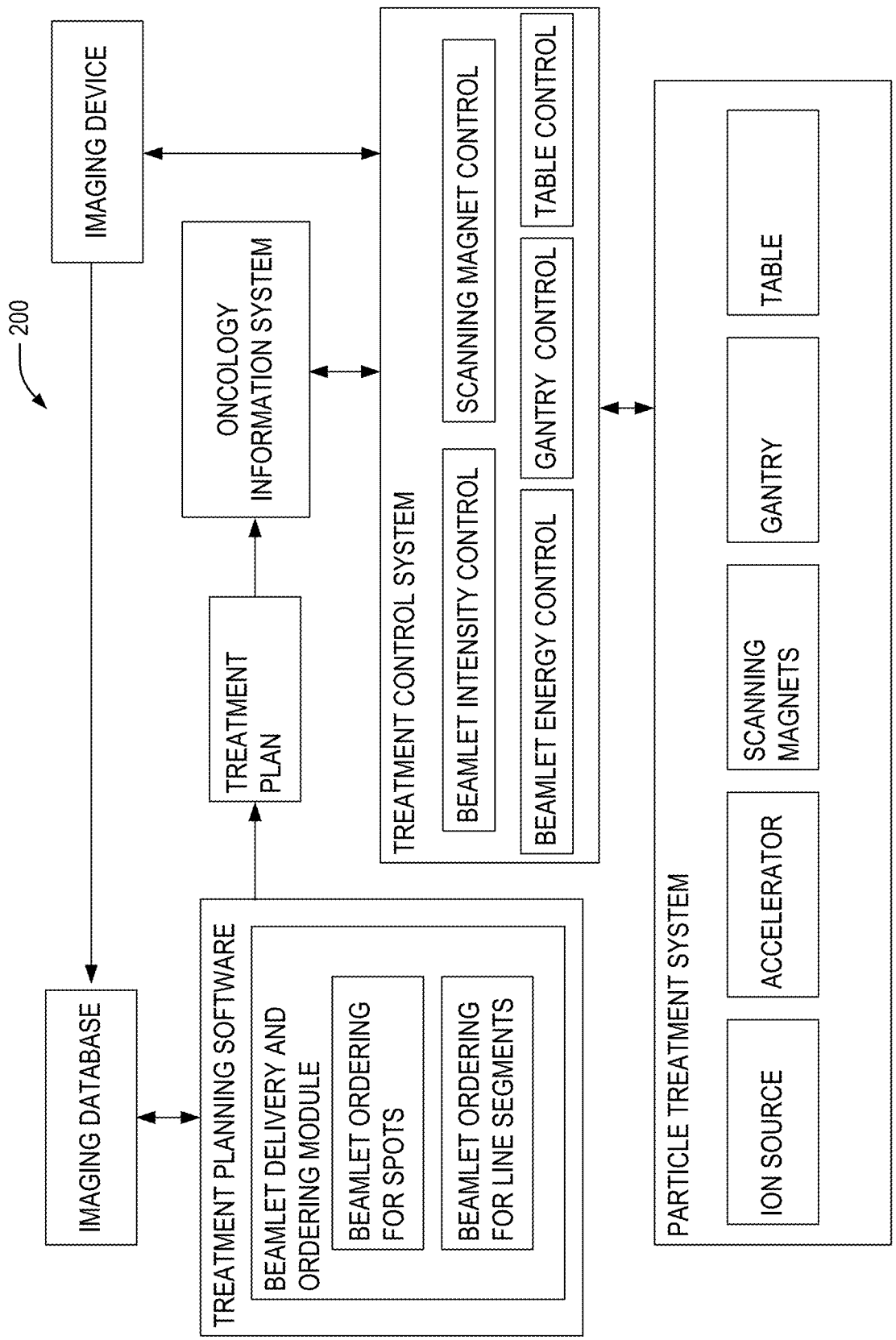
FIG. 2 illustrates generally an example of a radiation therapy system, such as may include a particle treatment system and an imaging acquisition device, in accordance with an embodiment.

FIG. 2 illustrates generally an example of a radiation therapy system 200, such as may include a particle treatment system and an imaging acquisition device, in accordance with an embodiment. The particle treatment system includes an ion source, an accelerator, and scanning magnets, each of which is described in more detail below with respect to FIG. 3. The particle treatment system includes a gantry and a table, where the gantry may be mounted on the table, affixed to the table, or stabilized with respect to the table. The table may hold a patient. The gantry may be a rotating gantry, and may rotate with respect to the table (e.g., around the table) or with respect to the patient (and the table or a portion of the table may rotate with the gantry).

The particle treatment system may communicate with a treatment control system, which may be used to control actions of the particle treatment system. The treatment control system may communicate with an imaging acquisition device (e.g., to receive images taken by the imaging acquisition device or an imaging database) or an oncology information system. The oncology information system may provide treatment plan details to the treatment control system, such as received from treatment planning system. The treatment control system may use the treatment plan to control the particle treatment system (e.g., activate the gantry, the ion source, the accelerator, the scanning magnets, a particle beam, or the like). The treatment control system, for example, may include a beamlet intensity control, a beamlet energy control, a scanning magnet control, a table control, a gantry control, etc. In an example, the beamlet intensity control and the beamlet energy control may be used to activate a beamlet of a particular size or to target a particular location. The scanning magnetic control may be used to deliver beamlets according to the treatment plan, for example in a spiral pattern. The gantry control or the table control may be used to rotate the gantry.

The treatment planning software may include components such as a beamlet delivery and ordering module, with, for example, separate controls for beamlet ordering for spots or line segments. The treatment planning software is described in more detail above with respect to FIG. 1. The treatment planning software may access an imaging database to retrieve images or store information. When a treatment plan is completed, the treatment planning software may send the plan to an oncology information system for communication with the treatment control system.

Figure 3:
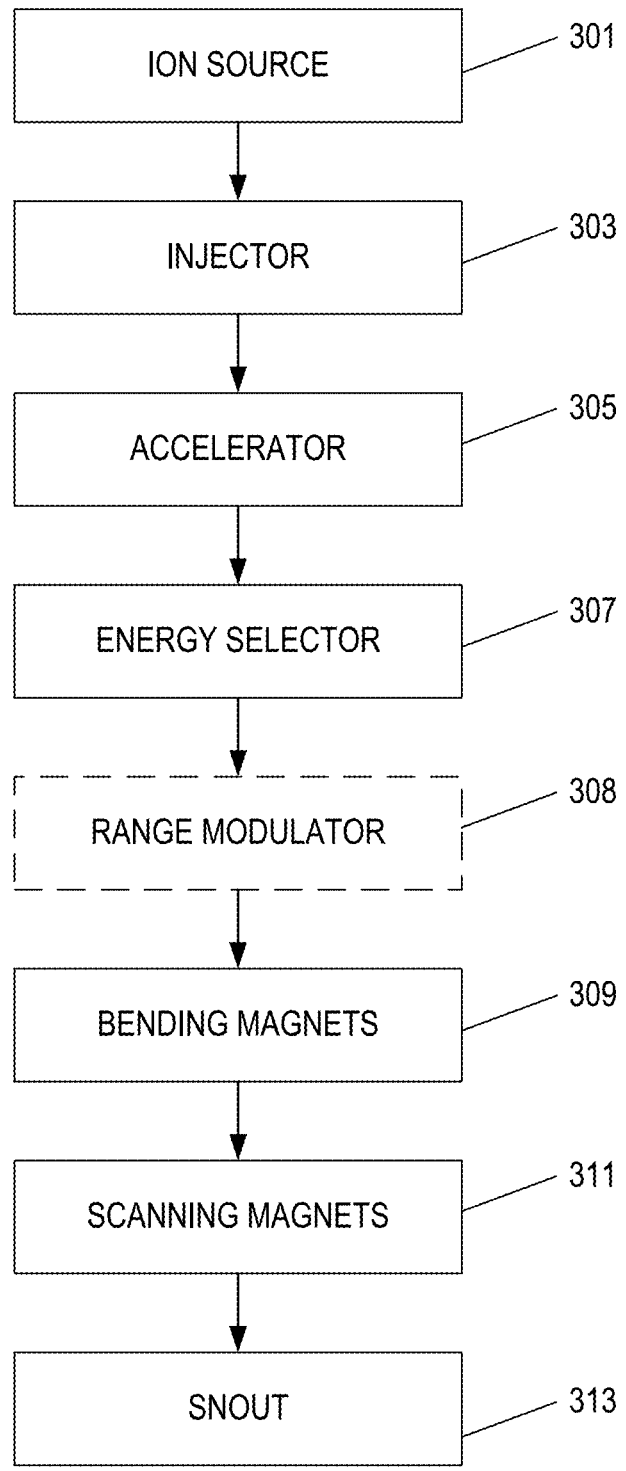
FIG. 3 illustrates generally a particle treatment system that may include a radiation therapy output configured to provide a proton therapy beam, in accordance with an embodiment.

FIG. 3 illustrates in an embodiment of a particle treatment system 300 that may include a radiation therapy output configured to provide a proton therapy beam. The particle treatment system 300 includes an ion source 301, an injector 303, an accelerator 305, an energy selector 307, a plurality of bending magnets 309, a plurality of scanning magnets 311, and a snout 313.

The ion source 301, such as a synchrotron (not shown) may be configured to provide a stream of particles, such as protons. The stream of particles is transported to an injector 303 that provides the charged particles with an initial acceleration using a Coulomb force. The particles are further accelerated by the accelerator 305 to about 10% of the speed of light. The acceleration provides energy to the particles, which determines the depth within tissue the particles may travel. The energy selector 307 (e.g., a range scatter) may be used to select the energies of the protons to be delivered to the patient. In an embodiment called passive scattering, an optional range modulator 308 (e.g., also called a ridge filter or a range modulation wheel) may be utilized to broaden the beam to fit the tumor. After selecting energies, a set of bending magnets 309 may be utilized to transport the stream of protons into a radiation therapy treatment room of a hospital. Further, scanning magnets 311 (e.g., x-y magnets) are used to spread the proton beam to, or trace, an exact image of the tumor shape. A snout 313 is used to further shape the proton beam. In various embodiments, the stream of particles may be composed of carbon ions, pions, or positively charged ions.

Figure 4:
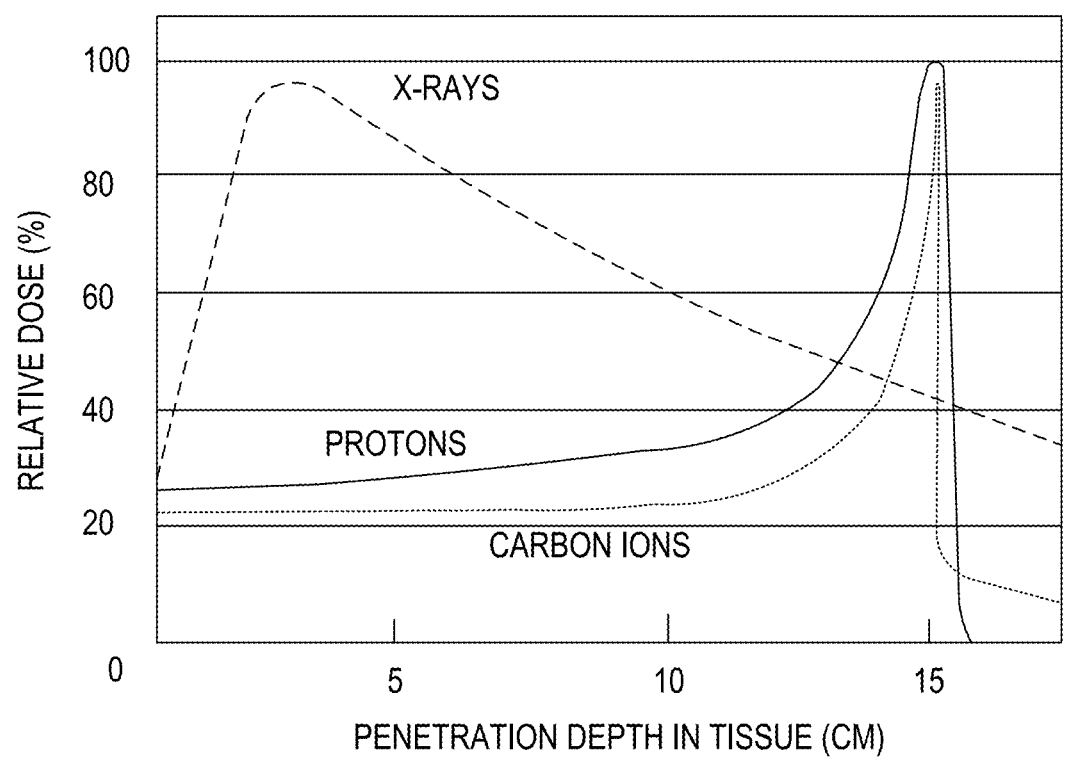
FIG. 4 illustrates generally radiation dose depths in human tissue for various types of particles, in accordance with an embodiment.

FIG. 4 provides an illustration of a comparison of radiation dose depths for various types of particles in human tissue. As shown, the relative depth of penetration into human tissue of photons (e.g., x-rays) versus protons versus carbon ions is provided (e.g., including any radiation dose provided at a distance beneath the surface, including secondary radiation or scatter). Each radiation dose is shown relative to the peak dose for a proton beam having a single energy which has been set to 100%.

The mono-energetic (e.g., single energy) proton beam indicates a plateau region starting at approximately 25% that gradually increases until approximately 10 cm depth in tissue where it rapidly increases to the Bragg Peak at 15 cm and then advantageously falls to zero within a short distance. No additional dose is delivered at the end of the Bragg peak.

The photon beam (e.g., labelled as X-rays) indicates the initial build up due to electron scatter (e.g., the primary means by which X-rays deliver dose to tissue is through transfer of energy to electrons in the tissue). This is followed by an exponential fall off, which continues past the distal edge of the target, which is at approximately 15 cm depth in the diagram. The x-ray beam has an entrance (skin) dose set to match that of the proton beam. With normalization (e.g., scaling) at 15 cm depth, the dose due to x-rays is at 40% of the dose provided by proton beam, while the x-ray beam has a peak dose of greater than 95% ("near" 100%) at approximately 3 cm depth. If the x-ray data is renormalized to achieve 100% dose at 15 cm, the peak dose at approximately 3 cm depth would be approximately 240%, in a location where dose is not desired (e.g., prior to the target). Therefore, with x-rays, a considerable amount of dose is delivered prior to the target and an appreciable amount of dose is delivered past the target.

The mono-energetic carbon beam shows a plateau region at the entrance dose that is lower than the proton beam. The carbon beam has a sharper Bragg Peak that falls more precipitously than the proton beam, but the carbon beam has a tail (e.g., known as a "spallation tail", where some of the Carbon nuclei shatter in to Helium ions) that has approximately 10% additional dose, or less, past the desired target by several centimeters. The carbon ion beam has an undesired entrance and skin dose compared to the proton beam, but the carbon ion beam has a non-trivial dose delivered past the target.

Figure 5:
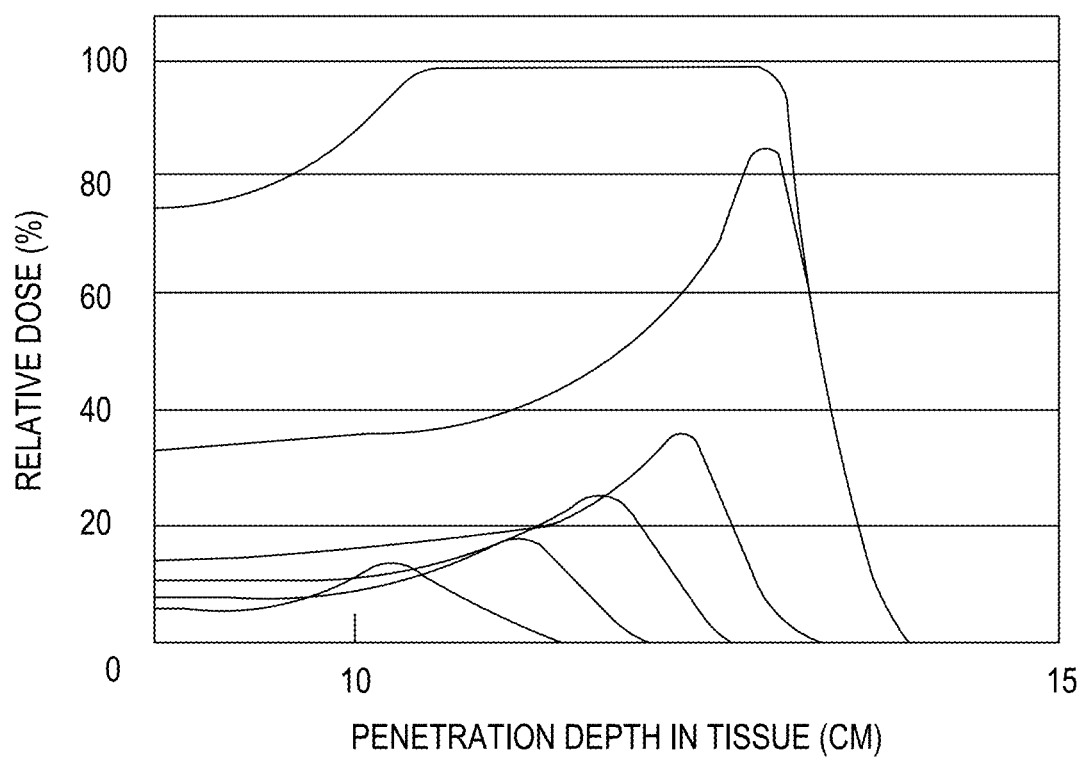
FIG. 5 illustrates generally a spread-out Bragg Peak, in accordance with an embodiment.

FIG. 5 provides an illustration of a spread-out Bragg peak (SOBP). The SOBP. displays a relative depth dose curve for the combination of a set of proton beams of various initial energies each of which has had some spread in energy (e.g., variable absorption of energy in tissue). The desired result of having a uniform dose for a target of a particular thickness. As shown, the target is shown with a proximal depth of approximately 10 cm, a distal depth of approximately 13 cm, and a target thickness of approximately 3 cm. Within the target, the dose is quite uniform (with an average normalized at 100%). The diagram does not start at 0 cm depth and is not explicitly showing the entrance (skin) dose, but the nature of the entrance region of proton beams is a relatively flat depth dose curve. Typically, the entrance (skin) dose will be approximately 70% of the target dose (e.g., shown at the far right edge of the x-axis). A SOBP may be obtained using a variety of approaches, including using a scattered proton beam with modulation of the energy (variable absorption) utilizing a variety of devices (e.g., a static ridge filter or a dynamic range modulation wheel), or by selection of a number of mono-energetic proton beams that do not undergo scatter.

Figure 6:
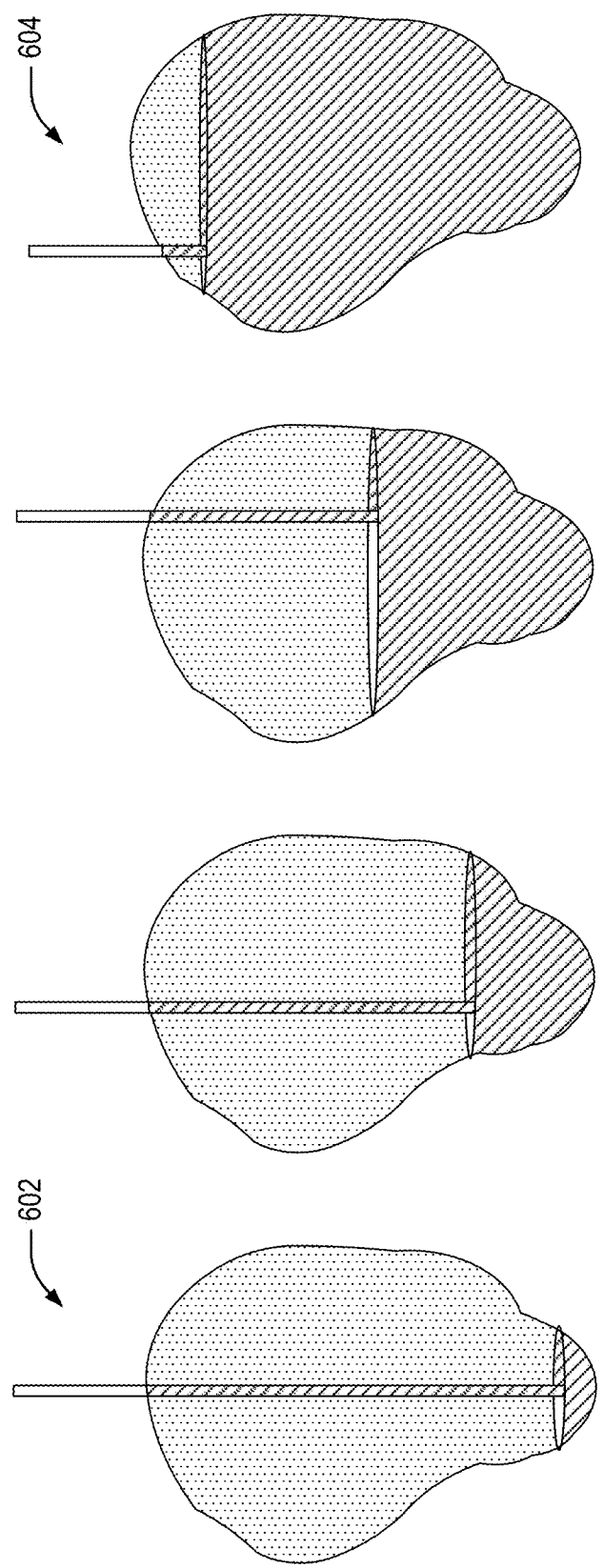
FIG. 6 illustrates generally pencil beam scanning of an irregular shape volume from distal edge to proximal edge, in accordance with an embodiment.

FIG. 6 provides an illustration of a Pencil Beam Scanning of an irregular shape volume from a distal edge (e.g., bottom) to a proximal (e.g., top) edge. As shown, the irregular shaped tumor volume is irradiated layers of protons. For example, a first time snapshot 602 shows a first layer of protons being delivered, and a later time snapshot 604 shows that most of the layers have been delivered. Each layer has its own cross-sectional area to which the protons having the same energy are delivered. The total radiation dose is provided as a layer-by-layer set of beamlets. Each layer of may have different energies. The most common means of specifying and delivering the set of beamlets to the cross-sectional area is to define and deliver beamlets having a constant diameter ("spot size") to a selection of grid points on each layer. While the majority of the dose from the beamlet is delivered to the targeted layer, a significant amount of dose is delivered along the path to the targeted layer. The dose to proximal layers from beamlets defined for distal layers is accounted for in the specification of the beamlets defined for the proximal layers. The ability to individually specify the number of particles (e.g., the meterset) for a given beamlet ensures that each part of the volume being irradiate receives the desired dose.

Figure 7:
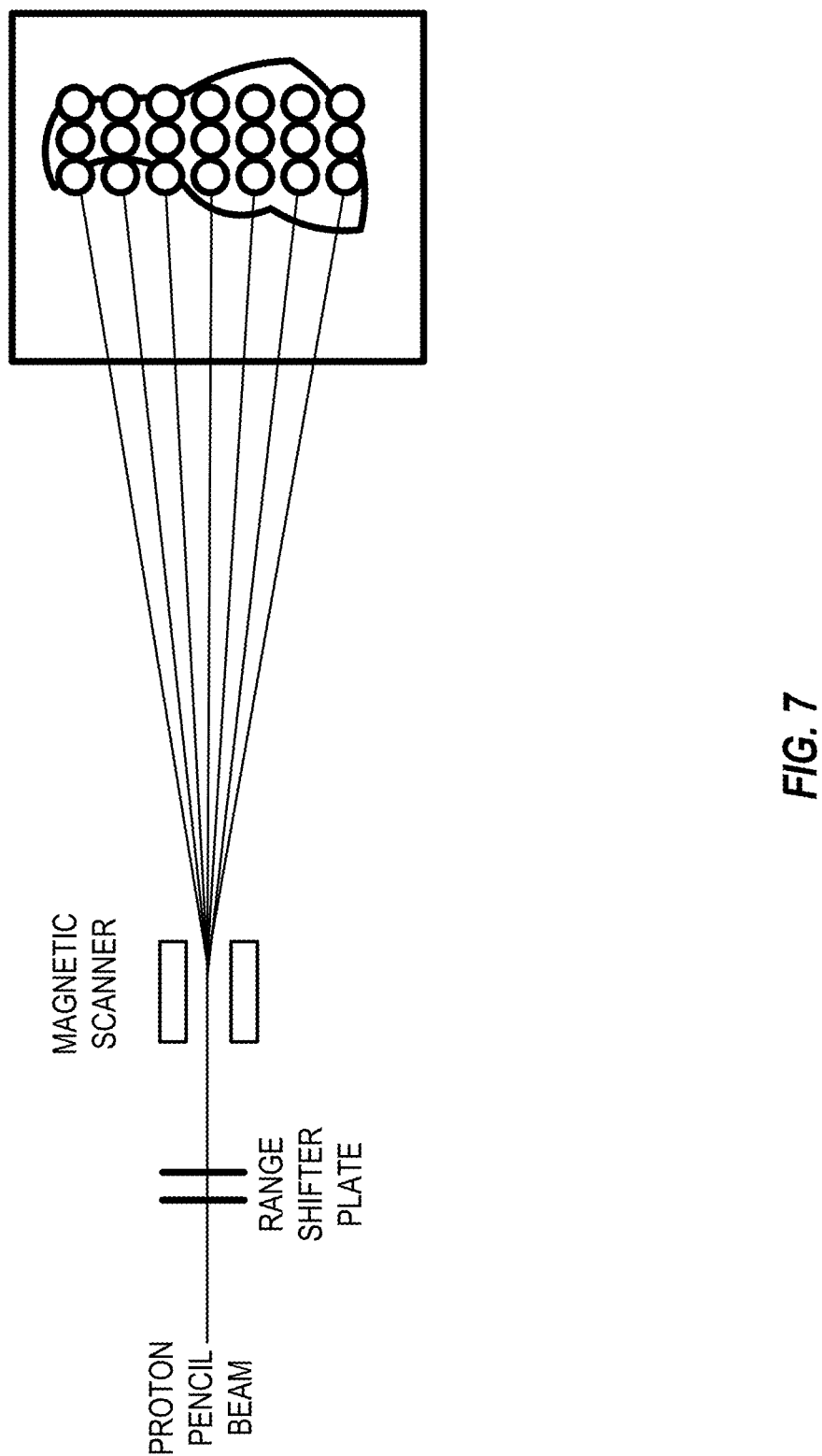
FIG. 7 illustrates generally a diagram of an active scanning proton beam delivery system, in accordance with an embodiment.

FIG. 7 provides an illustration of a diagrammatic representation of a typical active scanning proton beam delivery system. As shown, a single layer of a pencil beam scan is being delivered, with a grid of spots depicted on a patient in conjunction with a contour of the cross-sectional area to which particles are to be delivered. An incoming monoenergetic proton beamlet has a specified amount of its energy absorbed by the Range Shifter (e.g., in FIG. 7 it is a Range Shifter plate), resulting in a beamlet with the desired energy to achieve a certain depth for the Bragg Peak in the patient to treat the specified layer. A magnetic scanner, which has the ability to deflect the particles in both a vertical and a horizontal direction. The strength of the magnetic fields may be adjusted to control the deflection in the direction perpendicular to the magnetic field and the incoming beamlet. The rate at which the magnetic field strengths may be adjusted determines the rate at which the scanning may take place. For example, the intensity of the proton beamlet in combination with the scanning rate determines how much dose may be delivered to a specific area (e.g., in FIG. 7, a "spot") in a particular amount of time (e.g., particles/unit area). In theory, the magnetic field strengths may be adjusted independently of each other (in a fashion similar to the children's toy "Etch a Sketch®", provided by Spin Master™, Toronto, Canada; with the pencil beamlet intensity being a variable not available in the children's toy). The most common scheme for scanning is to scan in one direction quickly and to scan in the perpendicular direction more slowly in a raster fashion, similar to how early televisions were controlled (e.g., Cathode Ray Tube (CRT), which use electrons instead of protons), but arbitrary patterns may be scanned (similar to the previously mentioned toy). Delivery of distinct spots is achieved by incrementing the scanning magnetic field strength and throttling the pencil beam intensity between increments.

Cancer is one of the ten leading causes of death in the world. One method to treat cancer is radiation therapy, whose central component is treatment planning software that mathematically optimizes the radiation dose. In conventional particle therapy (e.g., proton therapy), a patient is irradiated from a few preselected directions. Each irradiating direction corresponds to a proton beam with multiple energies defining energy layers to control the depth at which particles deposit their energy and multiple thin particle spots within these energy layers defining the lateral beam extension. Particle spots are delivered using scanning magnets that define their lateral position. This method is known as pencil beam scanning. The spots within a beam scan a section of a target following a precise trajectory, thereby treating the tumor volume in a series of energy/range slices. A spot is typically defined by a point in the beam coordinate system for a given energy layer. The amount of radiation passing through a spot is measured in MU or number of particles. Thus, if the total beam MU or number of particles is known, an equivalent quantity is the relative spot weight associated with each spot. The weight describes the fluence of radiation for a given beam energy. Each spot weight can be independently varied to create a modulated fluence. Typically, the beam energy is modulated and grouped into several energy layers, so that varying the energy of a beam a broad coverage of the target tumor is possible. A beam may require many energy layers because the number of energy layers is roughly proportional to a tumor's size, for a Bragg peak (high dose region at the distal end of a particle spot) only covers a certain depth range. Thus, during treatment, it is necessary to switch from different energies within a beam and between beams.

Intensity modulated proton therapy (IMPT) currently uses an active spot scanning technique. A proton pencil beam can be scanned magnetically in two-dimensional directions perpendicular to a beam direction to form an irradiating field. Monoenergetic pencil beams, each with different energies, can be used to produce a desired dose distribution to "cover" a three-dimensional tumor target. By individually modulating the intensity of each scanning spot, an IMPT plan can be delivered. The proton scanning scheme can be continuous or discrete. In a continuous scanning system, a beam is swept in a raster like manner, whereas in contrast, a discrete scanning system uses a stop-and-shoot processes where the irradiating proton beam is turned off between spots. Typically, proton beams range from 4 cm to 20 cm in steps of 1 mm for lower energies and up to 6 mm for higher energies. The intensities for all proton scanning spots can be modulated independently. Therefore, only a minimum MU constraint is required to guarantee the deliverability of IMPT spot scanning.

Typically, the positioning of spots in a treatment plan is predetermined to cover the tumor target volume; and for all energy layers, a set of discrete spots is located with a predetermined defined space between the spots. In an example smaller spot spacing increases the dose homogeneity and lowers the organ-at-risk (OAR) dose, but smaller spot spacing also results in a number of low-intensity spots and reduces the treatment plan optimality. When designing a treatment plan, a threshold value for spot scanning is set to determine any trade-offs between the dosimetric advantage and the delivery constraints.

A monitor unit (MU) is a measure of machine output of a proton accelerator. There are minimum monitor unit (MU) constraints/limitations for delivering each pencil beam (e.g., spot) for the spot scanning system. A MU is defined by a fixed number of output pulses and one MU value is used to represent spot intensity. To ensure delivery accuracy, the minimum MU is set according to: 1) the spot dose should be higher than the expected delayed dose, and 2) the accuracy of the spot position can be reduced if a lower MU is used.

Particle arc therapy (e.g., including protons or carbon ions) can utilize the benefits of larger solution space (many irradiation angles and energies) to find a good treatment planning solution to achieve good target dosimetric conformality (e.g., a high, uniform does in the target volume), organ-at-risk (OAR) sparing (e.g., a low dose in surrounding organs), and improved delivery efficiency comparing to conventional static beam particle therapy with smaller solution space due to limited irradiation angles. Advantage of arc therapy include more angles, but also the convenience of beam setup.

A treatment planning system determines the energy layers and the spot dose deposition positions. The optimization process is used to find out the weights for all spots. The summation of all spot doses is conformal to the target and spare organs-at-risk. The increased solution space of particle arc compared to IMPT with a few particle beams having static angles typically leads to longer optimization time. Several methods have been proposed recently to solve the arc problem, which require iteratively coupling the arc sequencing and fluence (e.g., MU) optimization steps.

A general disadvantage of existing methods is the inefficient workflow with the optimization process performing on top of very large solution space. This means for example the dose calculation and fluence optimization is needed for many potential proton spots that will be not part of the final delivery plan (e.g., lack of treatment planning efficiency). In addition to that, the existing methods optimize the delivery efficiency in a limited way, for example typically only considering energy layer number or energy layer changes. The lack of including all relevant delivery properties in proton arc also leads to lack of the capability to get the optimum delivery time.

The systems and methods described herein include a novel and efficient particle arc treatment planning solution. This efficient workflow includes a powerful arc sequencing (spot pre-selection) section and a reduced fluence optimization section. Typically, a fluence optimization is initially performed for a set of initial spots. Then new spots (in existing or new energy layers or beam angles) can be added or removed. The fluence optimization is performed again. This process is iteratively repeated until the user accepts a satisfactory fluence optimization result. Alternatively, a large group of all potential spots is created initially and then most of them are removed during fluence optimization iteratively. This typical iterative process takes time, for example dose calculation and fluence optimization needs to be performed for many spots that will be excluded from the final plan. In case of pre-calculating all potential spots the additional problem of memory limits arises (e.g., not enough RAM memory available to store all spot dose distributions).

Another disadvantage of existing methods is lack of delivery parameters considered during optimization leading to less efficient solution in terms of total delivery time. Typically only the energy switching or total number of energy layers is penalized or considered while other parameters like number of spots (total or per layer), spot positions, scanning speed, delivery uncertainties leading to safety margins and need of spot rescans, gantry speed (with limits) and acceleration/deceleration properties are not considered. In the systems and methods disclosed herein, these parameters can be considered within the arc sequencing section (with some uncertainty margin as the final spot fluence is not known during sequencing). The knowledge of hardware specific parameters also allows to calculate the delivery time for each spot and thus correlate spot position and gantry angle (exact gantry angle can be approximated for dose calculation before optimization and is accurate for dose calculation after fluence optimization when all spot weights are known). With the systems and methods disclosed herein, dose for each spot at the delivery angle or approximate by one angle for all spots within one energy layer or within a part of an energy layer may be calculated.

The arc sequencing section and fluence optimization section may be decoupled. In an example, delivery and patient properties, planning preferences, such as target high dose region coverage by a certain number of paints, OAR sparing level, predicted robustness, target(s) shape/distribution complexity and angular dependent target subregion selection, delivery efficiency prediction, and the like may be used. An efficient arc trajectory may be found using these properties (e.g., a sequence of angles, energies, and spot positions) without the need of dose calculation and fluence optimization. Once the suitable arc trajectory is found, the selected potential optimum spots characterized by energies, angles, and positions are transferred to fluence optimization. No iterative process between the two sections is needed (e.g., the techniques described herein may be performed without iterating between the two sections or without returning to the arc sequencing section once working on the fluence optimization section). The fluence optimization section may be any classic or advanced fluence optimization algorithm (e.g., including Linear Energy Transfer (LET) or robust optimization) with optional extension of delivery time optimization. There is no restriction on devices that can be used for the particle arc techniques described herein, for example all devices from conventional particle therapy can be selected (e.g., range shifters, ridge filters, apertures, multi-leaf-collimators, compensators, bolus, or the like).

Figure 8:
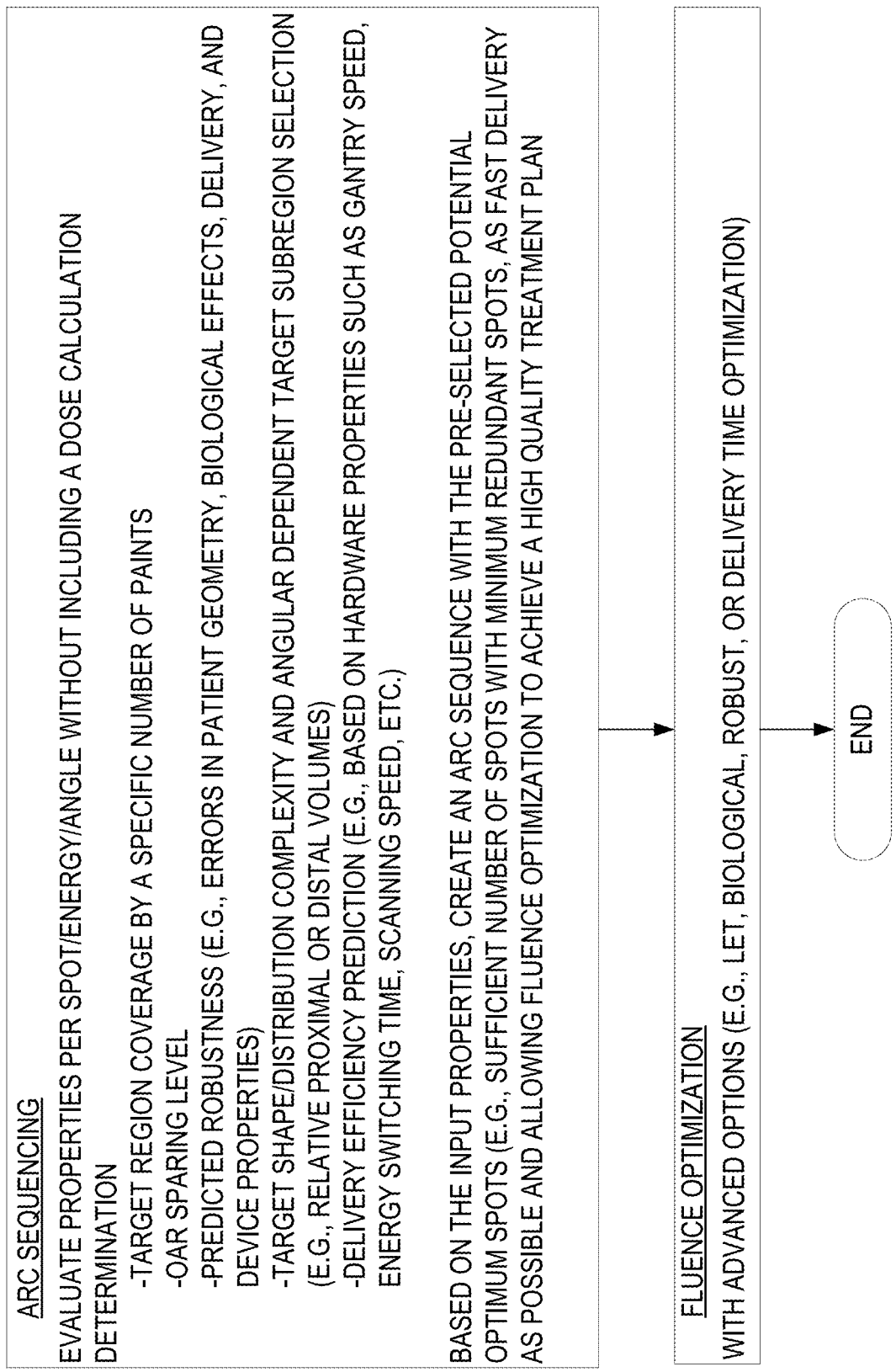
FIG. 8 illustrates a flowchart showing a technique for arc sequencing and fluence optimization, in accordance with an embodiment.

As described above, the particle arc technique described herein is decoupled into two sections: 1) arc sequencing and 2) fluence optimization, as shown in the flowchart in FIG. 8.

Before starting to solve the arc treatment planning problem, a preferred arc range may be defined (e.g., automated, based on templates, specified by treatment experience, etc.) and special planning preferences like target paint refers to how often a voxel is "hit" by a high dose region of a spot. Standard proton therapy is provided in energy layers. In these layers are thin spots with high dose regions restricted laterally and longitudinally (e.g., Bragg peak region) just before the end of their range. When a voxel is painted it means that the voxel has received high dose from a spot. Two paints means that the same voxel is within high dose region from two spots from at least two different angles, and so on. These may be taken into consideration during arc sequencing.

In the arc sequencing section, significant effort is made to find a solution space based on ray tracing data and hardware properties without having to rely upon cumbersome iterative dose calculation and fluence optimization. In an example, dose calculation may be performed after sequencing, as a first step of fluence optimization. First, effective properties for arc sequence quality evaluation are identified, which, for example, may be target coverage, OAR sparing, robustness, or the machine hardware itself. These properties may be per spot, per energy, or per angle. Based on such properties, the planning preferences can be applied, and the quality of a filtered solution space can be evaluated. By adopting a proper solving method (e.g., an analytical method, an automated algorithm or a hybrid method), a potential optimum set of spots (sufficient number of spots with minimum redundant spots, as fast delivery as possible and allowing fluence optimization to achieve a high-quality plan), which fulfils the planning preferences can be found.

Figure 9:
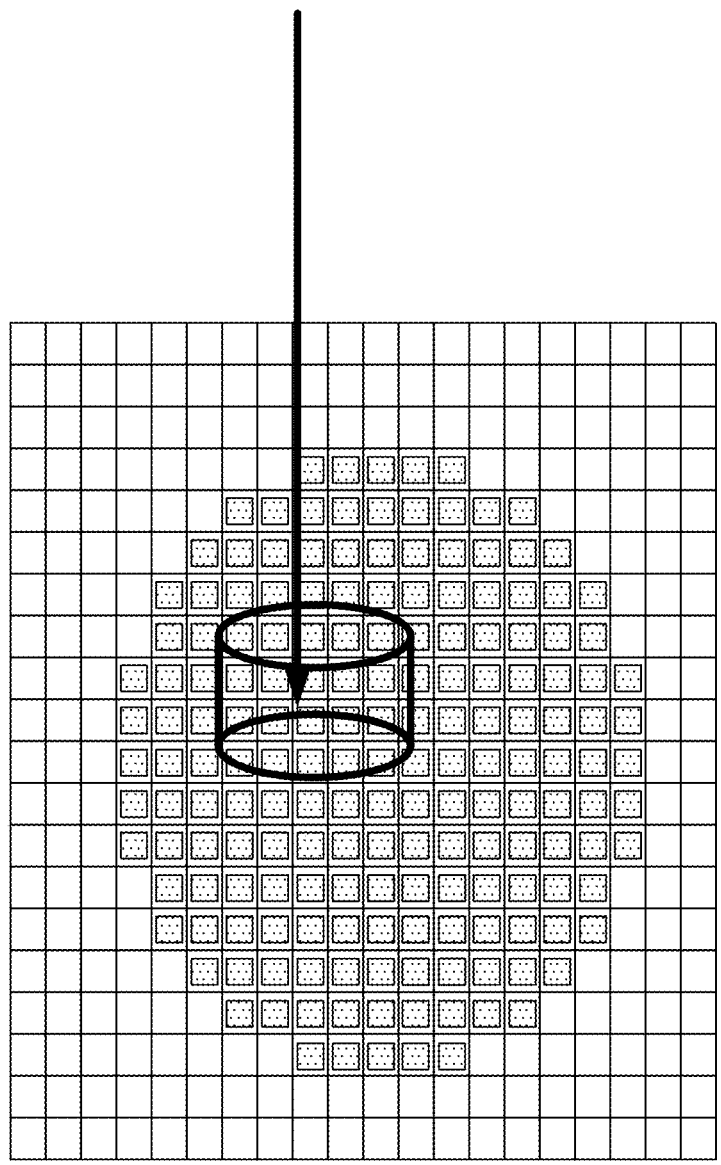
FIG. 9 illustrate arc angle target location intensity and Bragg peaks for various angles, in accordance with an embodiment.

In an exemplary implementation, the quality of solution space can be evaluated based on the target coverage. Target coverage is a sum of target coverage regions of all or selected spots. The target dose coverage region of one spot represents a volume within target within a high dose region around the Bragg peak of this spot. It can be, for example, defined as its Bragg peak center, and the approximate Bragg peak size. When a target volume becomes part of a target coverage region, it is painted one time. For example, in FIG. 9, the arrow points to the Bragg peak center and the cylinder indicates the Bragg peak size which is defined by spot size in lateral direction and interval of +/−80% of maximum dose in depth direction. All voxels within the cylinder are considered painted by this spot. By summing the total painted number per each voxel from all spots (from different positions, energies and angles) within the solution space, the target coverage regarding a certain number of paint can be evaluated and adopted as one property to describe the quality of given solution space. Alternatively, other geometric or precalculated shapes representing the Bragg peak region (shifted cylinder, sphere, 3D Gaussian, etc.) can be used and voxels can be attributed coverage probability instead of integer number of paints. In a similar way target coverage of quantities other than dose can be performed. For example, higher LET target coverage might be either joined by same coverage shape as used for dose coverage or use a different representation (e.g., LET coverage around the distal end of Bragg peak region when dose coverage is centered around Bragg peak).

Figure 10:
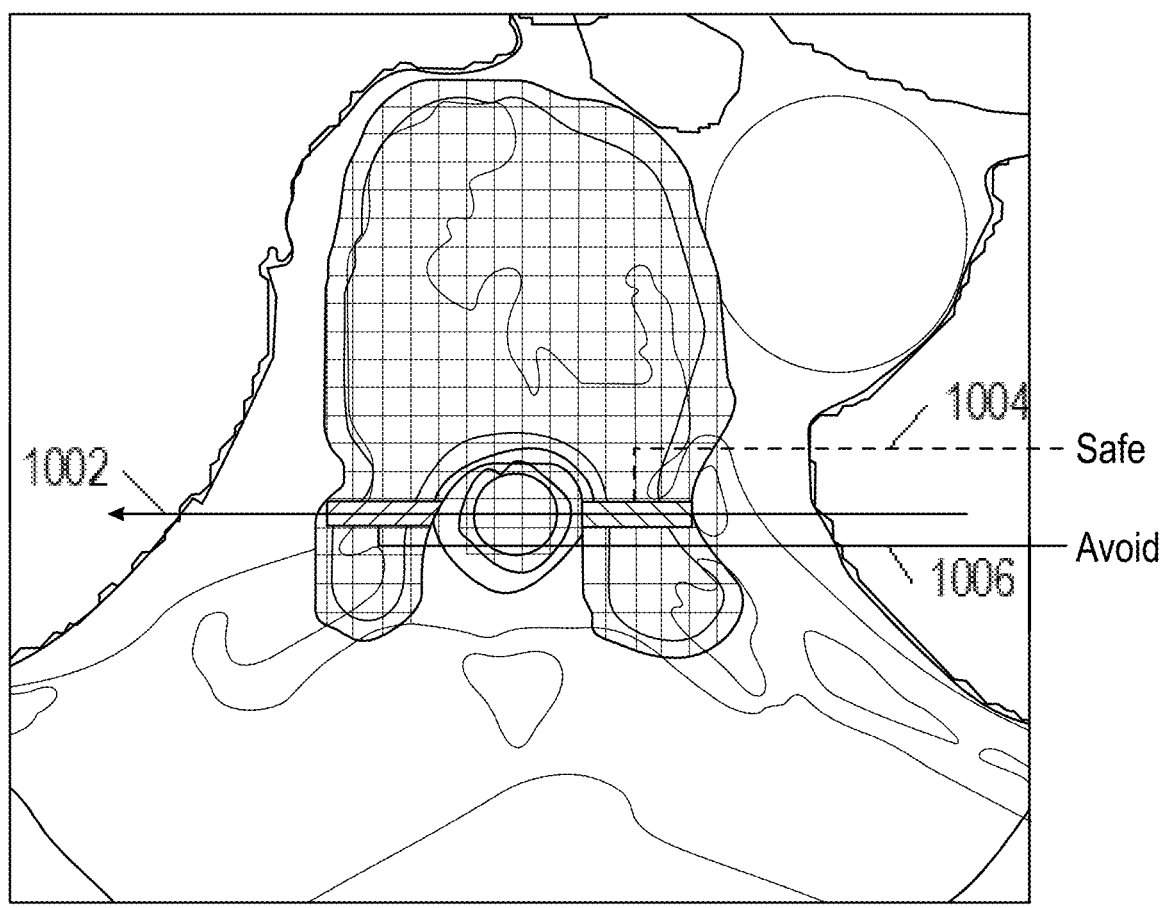
FIG. 10 illustrates generally a visualization of organ at risk and ray tracing, in accordance with an embodiment.

In extension to previous implementation or another, the quality of solution space can be evaluated by OAR sparing level. According to the ray tracing result, it is possible to know whether a ray or a spot is hitting or stopping in an OAR. For example, given a patient anatomy grid including target and OAR area information, performing ray tracing along the spot direction the ray can see anatomy information voxel by voxel. Once a ray hits any OAR voxel (or passes in close distance to OAR) before it hits a target voxel, this ray can be flagged as hitting an OAR. Or, the ray tracing result shows Bragg peak region of a spot is within an OAR area, then this spot can be flagged as stopping in an OAR. The quality of solution space can be evaluated in terms of sufficient OAR sparing by counting how many spots within the solution space are hitting or stopping in an OAR. FIG. 10 shows an example of spine as a target and spinal cord as an OAR, an arrow 1002 indicates a ray which passes through part of the target, then through the OAR and finally through other part of the target. The spots stopping within first part of the target can be treated as safe spots (region pointed to by 1004) while the spots within the second part of the target could be removed from the solution space (region pointed to by the line 1006).

In extension to previous implementation or another implementation, the quality of solution space can be evaluated in terms of robustness. Treatment plan robustness normally means the degree to which the desired dose distribution is resilient to some uncertainties like position shifting or density change due to patient setup, image quality and target movement etc. In order to predict the robustness without dose calculation, some approximations can be adopted. One example can be counting the percentage of rays from one angle passing through the couch edge (which leads to significant uncertainty because the sharp edge of the couch is sensitive to any position shifting) and if the number exceeds a certain threshold (threshold can be set to any value between 0 and 100%) than such angle may be removed from the solution space. Another example can be characterizing the level of lateral heterogeneities and then the angles or spots with heterogeneity index higher than threshold could be removed from the solution space. Another example can be characterizing the density change effects by shifting the Bragg peak region or high LET region by applying density uncertainty and remove spots stopping in a specified OAR.

Figure 11A:
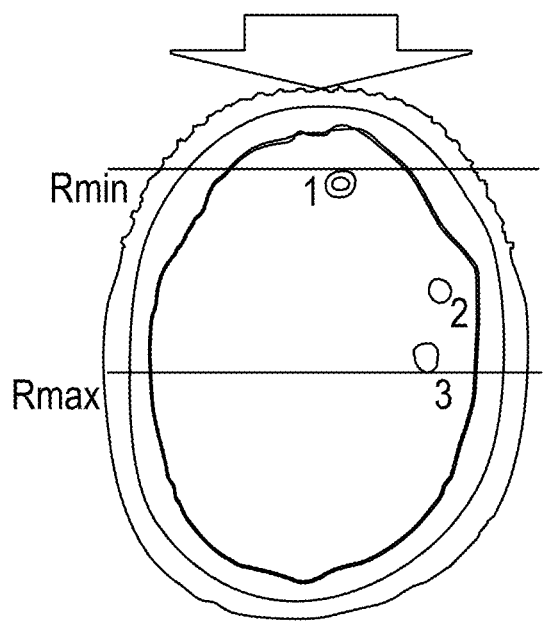
FIG. 11A illustrates a linear spot delivery path with differing spot sizes and a raster pattern, in accordance with an embodiment.
Figure 11B:
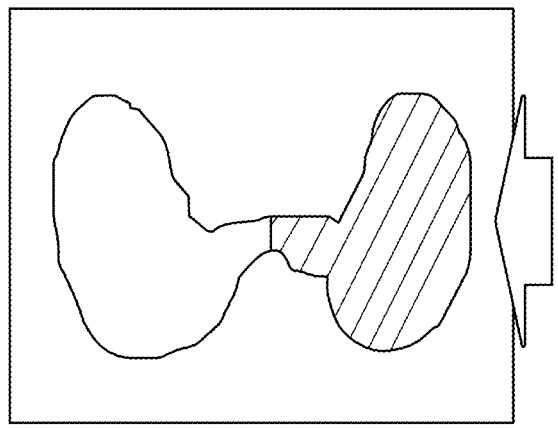
FIG. 11B illustrates a spiral spot delivery path with differing spot sizes, in accordance with an embodiment.
Figure 11C:
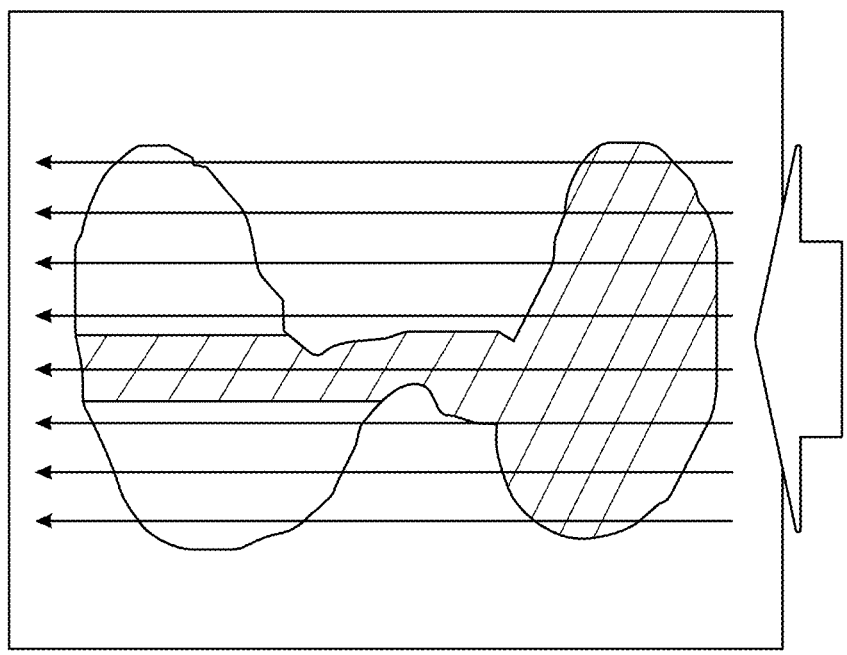
FIG. 11C illustrates a composite target location intensity, in accordance with an embodiment.

In extension to previous implementation or another implementation, one can restrict the solution space by considering the target shape complexity. For example, one can detect discontinuous or continuous target subregions in different range regions depending on the ray angle. According to different planning preferences, specific subregions can be removed from the target for certain spots within some angular intervals and thus restrict the solution space accordingly. To be more specific, for discontinuous target subregions, if one planning preference is for example set for first proximal (or last distal etc.) volume preference, only the first proximal (or last distal) subregions seen from one ray/angle are available. For example, in FIG. 11A for angle from top it may be target 1 only (or target 3 for last distal volume preference settings). The number of subregions can be also selected to be higher than one (both on proximal or distal target range). If no planning preference regarding to subregion selection is applied, this can mean none of the subregions get removed (e.g., in FIG. 11A all target 1, 2 and 3 are available). Planning preference can be also set to specific range interval, for example the X % proximal volume preference can mean X % of closer subregions are valid (in FIG. 11A, it could be target 1 and 2 with 70% preference). For continuous target, similar planning preferences can also be applied. For example, in FIG. 11B, only the first section of the target on the right is available (the shadow area) according to a 500% proximal volume preference. FIG. 11C illustrates similar settings as for FIG. 11B however with 50% proximal volume preference being applied only to discontinuous target subregions along the rays (thus depending on ray angles).

In extension to previous implementations or another implementation, the quality of solution space can be evaluated by delivery efficiency. Depending on accelerator type, switching nominal energies can be time costly, especially switching energies up. One simple example to evaluate delivery efficiency can be thus counting energy switching up times. On the other hand. Another simple example can be counting total energy switching times.

In an example, a set of spots is created based on specific settings including constant or dynamic spot placement. The spot placement may include lateral spot distance within an energy layer that depends on spot size or on placement within important target regions or within proximity to organ at risk.

A more comprehensive example to evaluate delivery efficiency can be considering as many hardware parameters and constraints as possible to calculate the approximate total delivery time. This may include taking into account energy switching times (can vary between up and down), spot scanning speed (can vary in x and y direction), maximum gantry rotation speed, etc. The total delivery time typically then consists of the time spent in one energy layer while gantry rotates (at optimized speed), time spent in switching to next energy (if needed) while gantry rotates (at optimized speed), time spent in next energy layer and so on. The time spent in one energy layer is calculated based on number of spots, their positions and order, number of spot or layer rescans and other delivery parameters and properties. Other hardware specific properties like gantry speed acceleration/deceleration, or the like may be considered.

The delivery efficiency can be adopted as an additional objective or penalty within the arc sequencing optimization. In such a way, it is possible to optimize both arc trajectory and hardware parameters (e.g., gantry speed within hardware limits) in order to minimize the total delivery time.

To find a potential optimum set of spots which fulfils the planning preferences, different approaches can be adopted. First, as a common step, a filtered solution space is created.

For example, in a typical brute force method, the target voxels are painted with radiation dose from each angle for all energy layers and spot positions. The solution space can be reduced by considering the set of painted voxels (voxels that are within a high dose or high LET region). By knowing that a voxel at location A is painted at angle X, this same voxel can be determined to not need a dose delivered, (e.g., painted), from a different angle Y. Therefore, this voxel may be removed at angle Y and the corresponding spot(s) at angle Y painting this voxel can be removed from the solution space, which reduces the solution space. Removing painted voxels at a different angle may be used to decrease the size of the solution space, which makes optimization more efficient as the solution space to be considered is smaller.

A second or more rounds of a previously painted voxel may be painted by a certain delay. Such delay may be properly selected to make sure one voxel does not get redundant irradiation from a similar angle, energy or spot position to the previous painting spot which will not produce a differentiable dose distribution. The delay can be defined by a sufficient angular space. For example, a voxel is painted at angle X, then the voxel can only be painted again after angle X+D where D is the desired angular delay. The delay can also be defined by a sufficient delay of time. In this example, a voxel gets painted at time X is only be painted again after time X+D in unit of second for example. In other cases, the delay can be given by the energy switch up cycle. This means a painted voxel can only be painted again when the hardware has performed another energy switching up after it received the previous painting. As the target volume changes depending on gantry angle we call this approach of removing or restoring parts of target (e.g., voxels) a dynamic target approach.

Figure 12A:
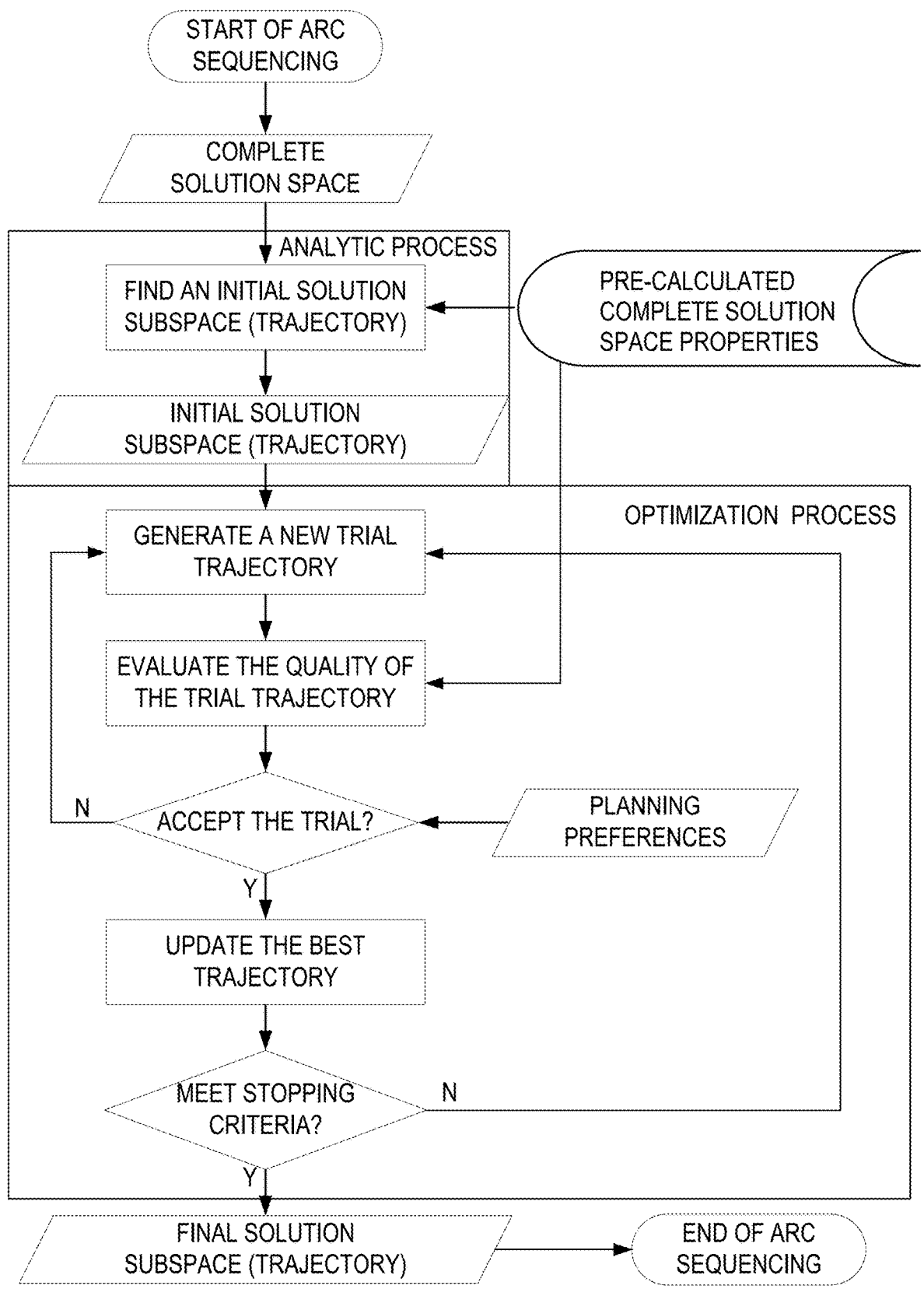
FIGS. 12A-12B illustrate flowcharts showing techniques for arc sequencing and fluence optimization, in accordance with an embodiment.
Figure 12B:
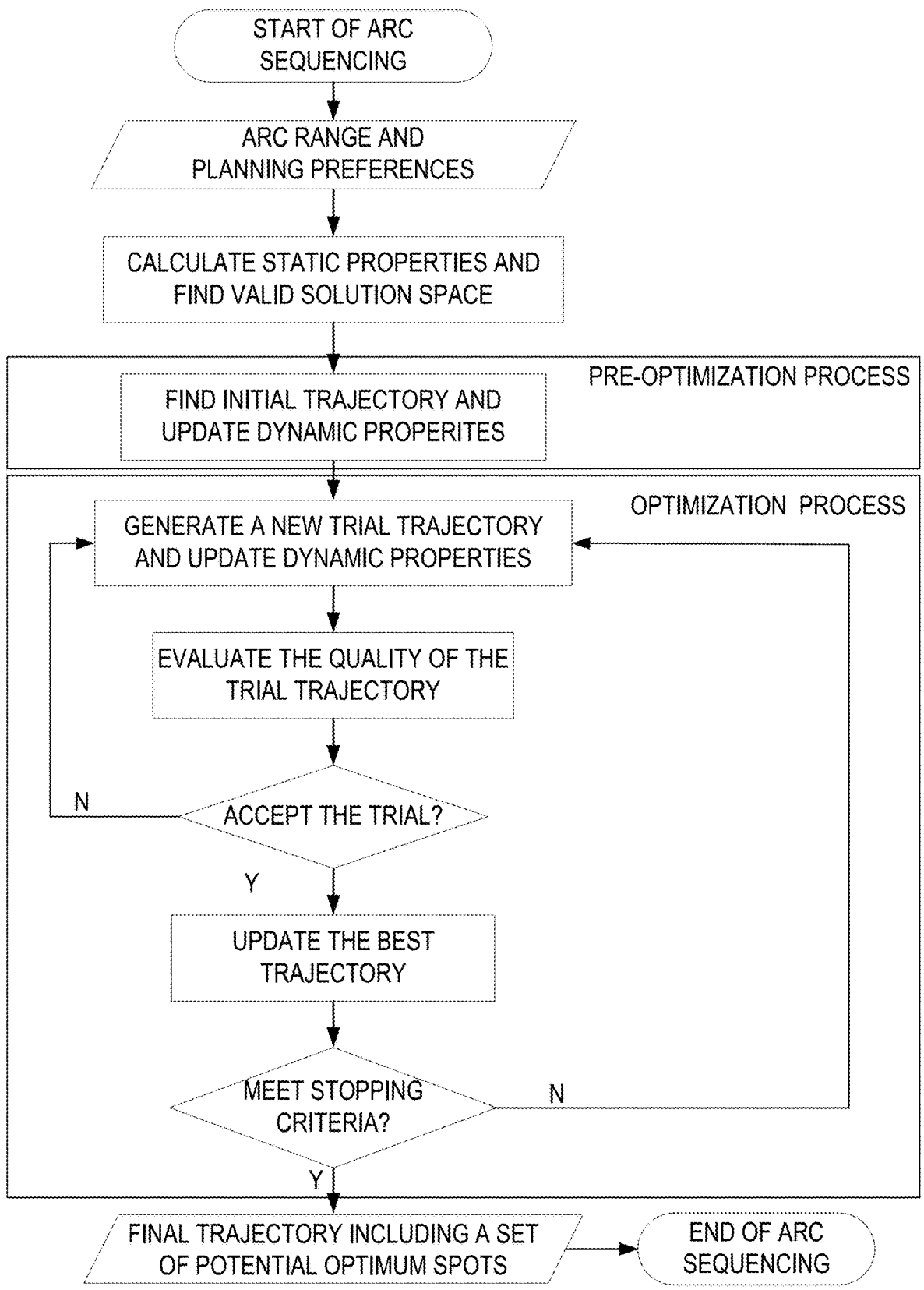

In FIGS. 12A-12B the arc sequencing flowchart is described. First a complete valid solution space (e.g., all potential spots/layers/angles) is identified (e.g., using fast calculation methods like ray tracing). Then different processes (such as pre-optimization or optimization) or their combinations can be used to identify the final solution subspace (arc trajectory). This subspace may then be input to fluence optimization.

In an implementation, a pre-optimization process of arc sequencing can be used. This can be based for example on an analytical solution, manually set solution, predicted solution (e.g., using artificial intelligence), etc. A certain number of settings can be applied, for example by 1) selecting one layer per one angle, 2) always decreasing the energy as long as spots from energy layer stay within target specified region, 3) applying evaluation methods or their combinations, such as objective target coverage, OAR sparing level, predicted robustness, target(s) shape/distribution complexity and angular dependent target subregion selection, delivery efficiency prediction, or the like. Based on such settings, a pre-optimization solution for the arc trajectory can be found. Pre-optimization operations may occur entirely before an optimization process or may be used without an optimization process. In some examples, a result of the pre-optimization can be used as input to optimization process. Thus, the optimization process starts with a reasonably good solution and can lead faster to an optimum arc trajectory.

In another implementation, an optimization process can be adopted (e.g., without a pre-optimization process) to find an optimum arc sequencing. Given an objective (can be defined by any of the quality evaluation method (e.g., target coverage, OAR sparing level, predicted robustness, target(s) shape/distribution complexity and angular dependent target subregion selection, delivery efficiency prediction, etc.) or a combination of multi-objectives, solving with an optimization algorithm (can be a global search optimization algorithm (e.g., a Simulated Annealing algorithm), an optimum arc trajectory can be found.

By filtering the solution space during arc sequencing the fluence optimization process is faster and more efficient. The weighting problem is typically more cumbersome because of the huge solution space that has to be considered. Arc sequencing provides a filtered solution space by considering suitable properties which are used to evaluate and make sure the good quality of the limited solution subspace. Using the smaller solution subspace, a user may find a comparable optimum solution from the subspace quicker, because the subset is well defined by arc sequencing. The fluence optimization is a general problem that can be solved by any classic or advanced fluence optimization algorithm. The fluence optimization is flexible and extends to different user intentions. To guarantee a deliverable plan fluence restrictions imposed by hardware properties (minimum fluence—MU or number of particles, maximum fluence, fluence resolution, etc.) are considered during fluence optimization following the conventional (IMPT) fluence optimization.

The advantage of this process is that there is no need to iteratively process between arc sequencing module and MU optimization techniques. Thus, this is a very efficient workflow. In the end, a desired plan is found within a reasonable planning time. While the result of sequencer can be used to calculate a rough delivery time estimate, the delivery time estimate is more accurate after fluence optimization as the real fluence distribution can be considered in delivery time calculation.

An arc sequencing visualization tool is introduced to show how the target coverage density of target water equivalent (WEQ) range is distributed (while satisfying certain planning preferences) across the full defined angular range and thus where the potential solution space can be.

Figure 13:
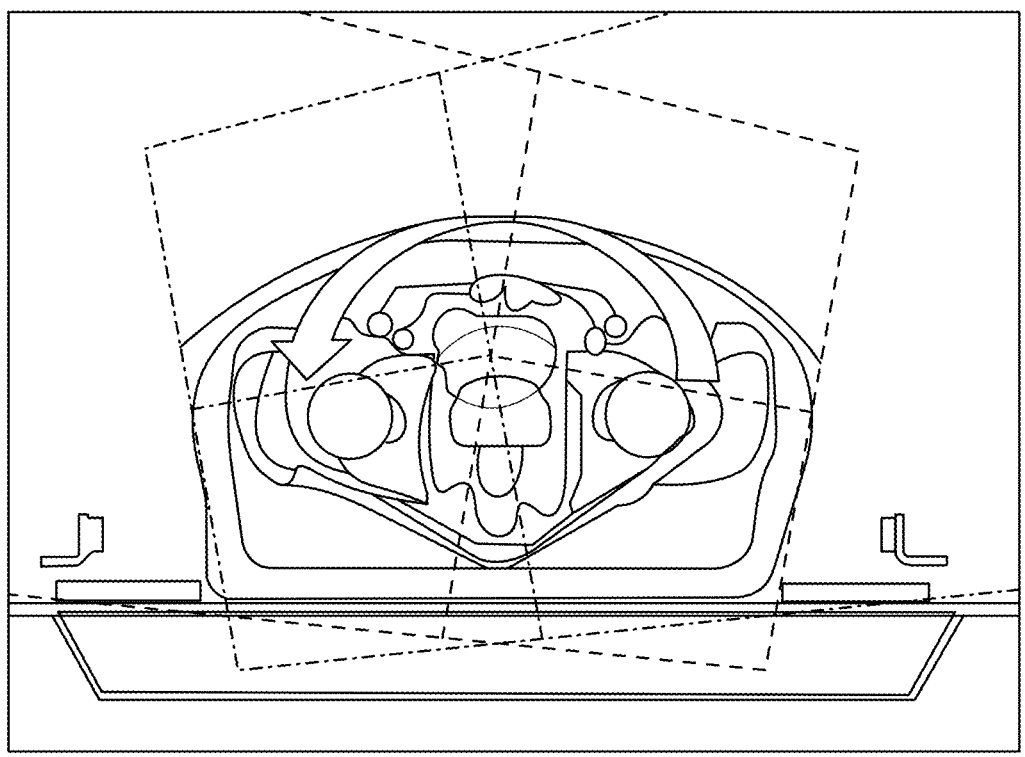

FIG. 13A is an example of prostate case, where the arc angular range is defined between +100 deg going clockwise to −100 deg.

Figure 14A:
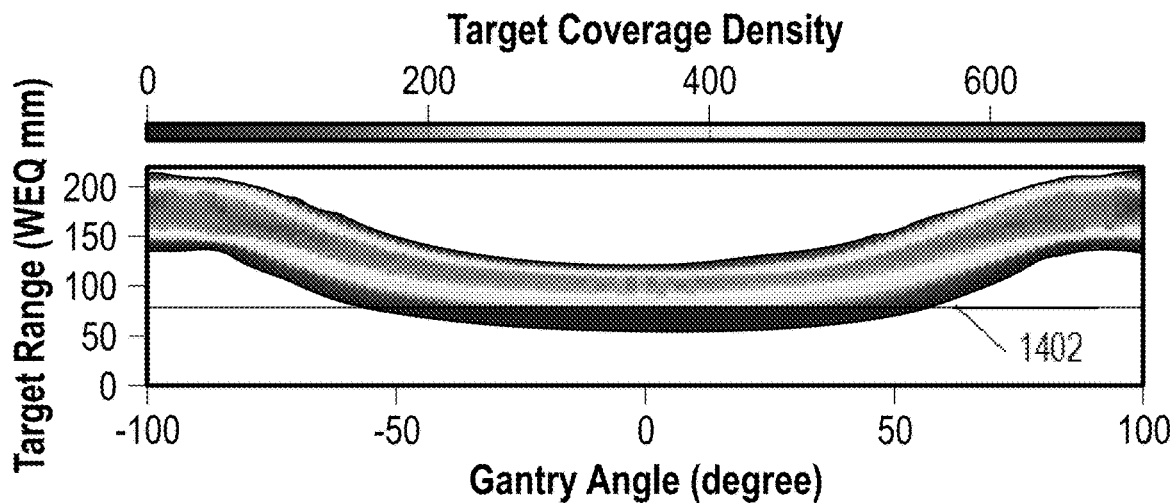

In FIG. 14A an example of the arc sequencing visualization tool is presented. It shows a colormap of target WEQ range distribution across all angles, the various shades indicate the target coverage density (e.g., number of painted voxels) at a WEQ range (energy) and angle. For example, the lighter shade in the central portion of the band indicates there are many voxels, fewer voxels outward towards the edges of the band from the center, even fewer voxels in the darker shades at the edges of the band, and darkest shade where the least number of voxels are painted. The outer edges of the band indicated by irregular lines indicate the minimum and maximum WEQ range of the target. Thus, the lower line of the band indicates the lowest WEQ range (energy) that can be provided to cover the target and the upper line of the band indicates the maximum WEQ range (energy). The horizontal line 1402 indicates the lowest WEQ range (energy) that can be provided by the hardware or set by user, which may be a hard constraint, and no more target information needs to be investigated beyond this lower energy limitation. The potential solution space can be displayed in between two lines of the band together with the restriction by the horizontal line 1402. The colormap may be taken into consideration to further reduce the solution space from less contributed points (for example where very limited or no voxels can be painted). Any point within such area can be a potential element of the arc sequence (e.g., a potential element of the solution space). The X and Y axis of the point represents the angle and WEQ range (energy) of the solution element.

Figure 14B:
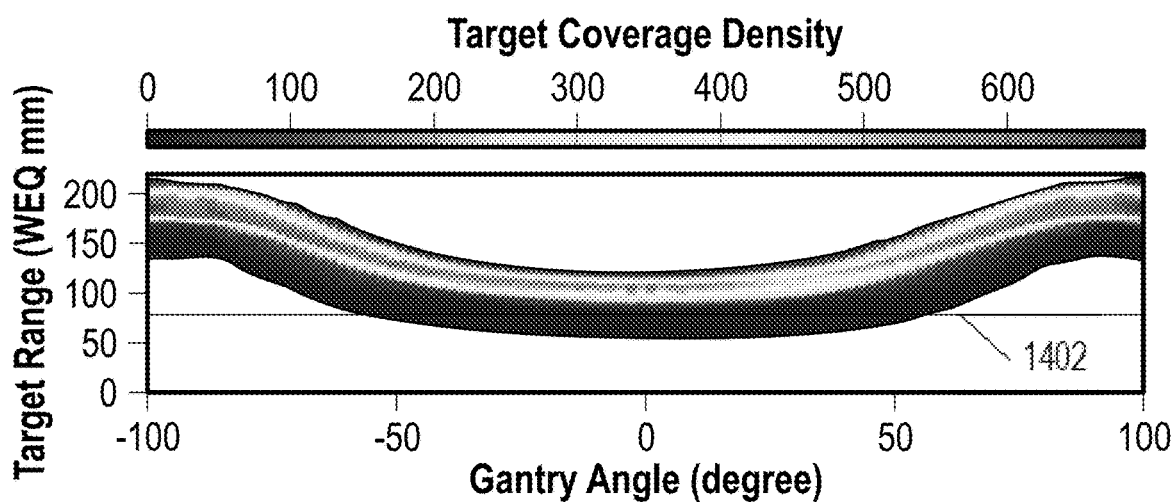

FIG. 14B shows an example of potential solution space of the same case with a 'the half distal volume' planning preference satisfaction. One can see in order to meet the specific preference, the potential solution space is reduced.

Figure 14C:
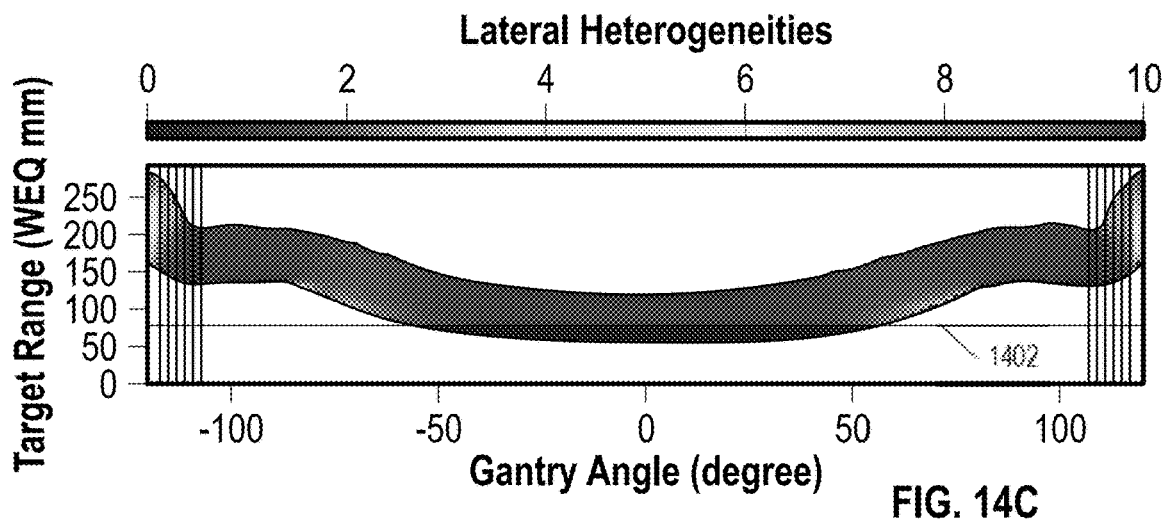

In FIG. 14C another example of the arc sequencing visualization tool is presented. Being Similar to FIG. 14A the two irregular lines forming the band indicate the minimum and maximum target range and the horizontal line 1402 indicates the lowest range that can be provided by the hardware or set by user. The colormap in FIG. 14C shows the predicted lateral heterogeneities of all ranges (energies) and angles within the complete solution space. The brighter the shade in FIG. 14C, the more lateral heterogeneous. Considering the colormap information, the solution space can be reduced from those with higher lateral heterogeneities. Also, around +/−110 degree there are two shadow areas represented by vertical lines. They indicate the couch edge avoidance area which means the angles within such area should be removed from the solution space due to concerns about the non-robust of those areas.

The arc sequencing visualization tool is not restricted to either target coverage density or lateral heterogeneities, a system may be configured to display one on top of another in the same figure. The system is not restricted to target coverage density or lateral heterogeneities, there can be other quantifications (e.g., OAR sparing info) applied.

An arc sequencing visualization tool is also introduced in FIGS. 15A and 15B to show how an exemplary arc trajectory can be selected and to provide an example of the quality of a determined arc trajectory. Each discrete dot (e.g., dot 1502) represents a layer at a particular energy and a particular angle (e.g. gantry angle), a sequence of such dots comprises an arc trajectory at energy layer level (complete arc trajectory also includes individual spots within energy layers). For example, in FIG. 15A and FIG. 15B, the arc trajectories start from the right end at angle 100 degree and the distal edge (the maximum WEQ range) of the target, then the trajectories go gradually down left to cover other voxels from different angles and WEQ ranges (energies). The trajectories can go up when energy is switched up. The energy switch up can happen at any properly or arbitrarily selected position to restart to paint the distal part of the target again. The colormap now shows a dynamic target WEQ range distribution according to the target high dose region painting state by the selected arc trajectory and the desired delay. One voxel can be counted on the dynamic distribution only after it meets the desired delay since it was previously painted.

FIG. 15A shows an exemplary worse arc trajectory than FIG. 15B in terms of delivery efficiency (delivery time is longer due to more energy switching ups). FIGS. 15A and 15B also show multiple curves (e.g., 1504A and 1504B) which represent the probability of target high dose region coverage with different number of paints, the value is labelled on the right axis scale in range between [0%, 100%]. For example, the solid curve 1504A corresponds to 3 times paint coverage, in FIG. 15A starting from 0% at around 65 degree and going up to around 80% at −100 degree. The same 3 times paint coverage is shown in FIG. 15B at curve 1504C with a coverage around 95% at −100 degree. Thus FIG. 15A represents a trajectory that is worse than the trajectory of FIG. 15B both in terms of delivery efficiency and target coverage in this example.

Figure 16:
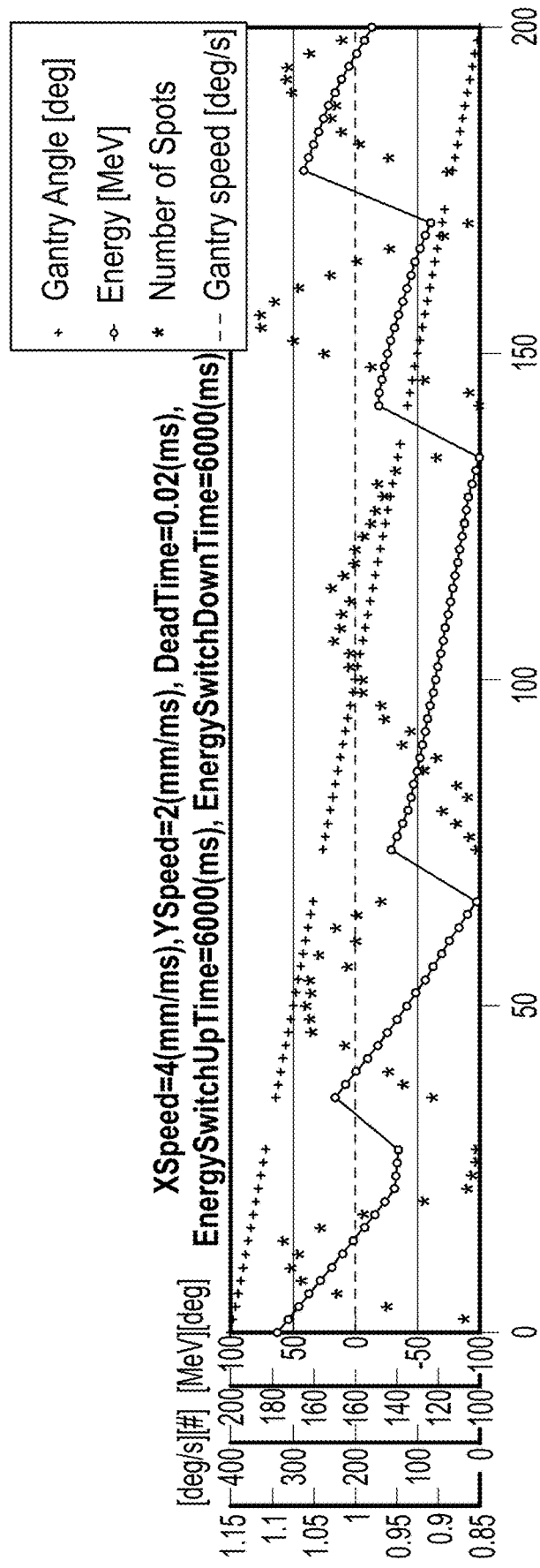
FIG. 16 illustrates a delivery profile visualization tool, in accordance with an embodiment.

A delivery profile visualization tool is introduced in FIG. 16 to simulate how the arc trajectory is delivered along with time. This can help the user to preview the arc treatment process and check if the delivery (e.g. total delivery time or gantry speed) is within expectation. As an example, FIG. 16 provides four types of delivery information all along with time labeled on x axis. The four types of delivery information are gantry nominal angle (marked as plus signs) labeled on the very right y axis, the layer energy (marked as circles) labeled on the second to the right y axis, the number of spots of current layer (marked as stars) labeled on the second to the left y axis and gantry rotation speed (marked as dashed line) labeled on the very left y axis. FIG. 16 shows the corresponding estimated delivery profile of the arc trajectory in FIG. 15B. By reviewing two figures together a good overview of the arc trajectory quality and efficiency is shown.

Figure 17A:
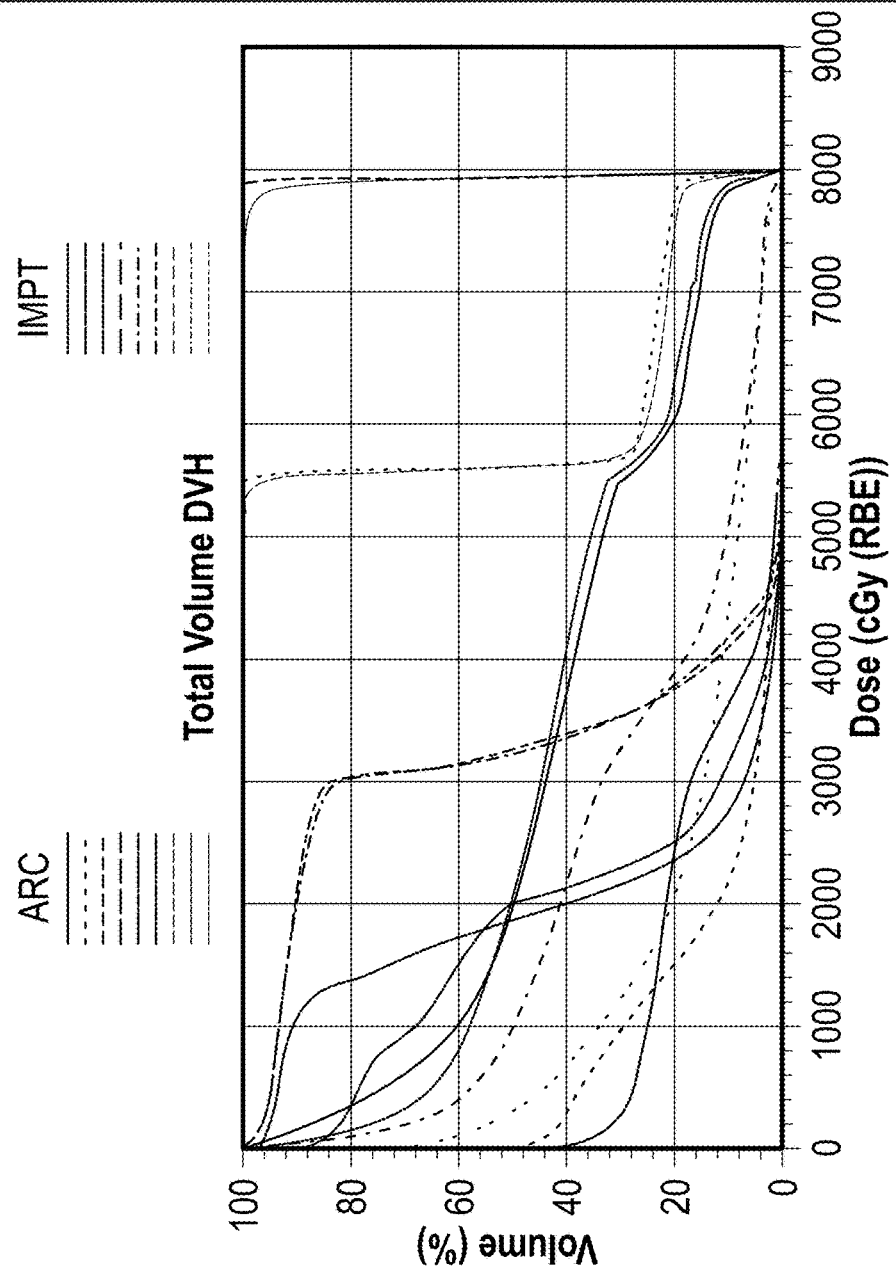
FIG. 17A illustrates a proton arc plan, in accordance with an embodiment.

FIG. 17A illustrates a proton arc plan for prostate node treatment generated by the present systems and methods versus a conventional two fields IMPT plan. FIG. 17A shows nearly equivalent target (PTV and CTV) DVH curves of arc plan and IMPT plan while preserving more OAR volumes which means the proposed solution can create a qualified arc plan.

Figure 17B:
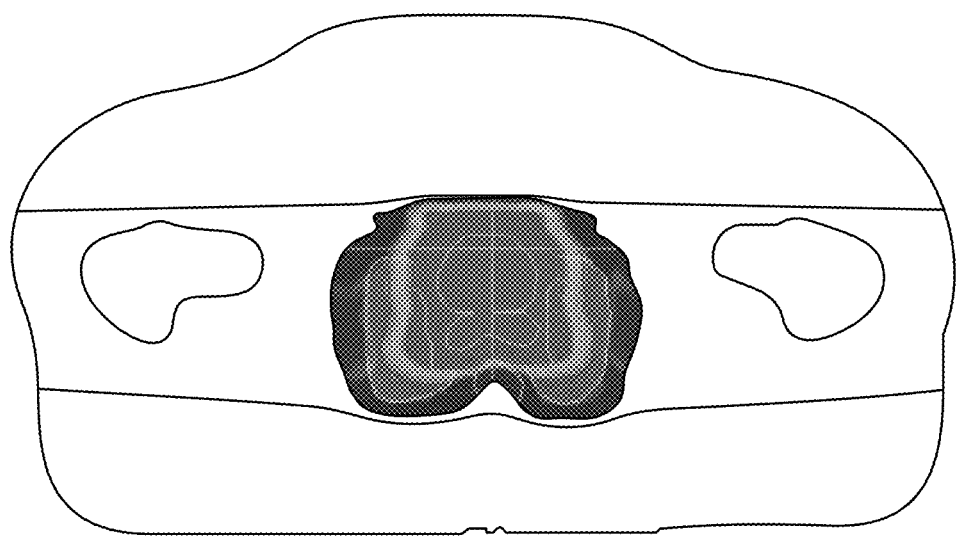
FIGS. 17B-17C illustrate 2D target dose distribution on the same slice of two fields in an intensity modulated proton therapy (IMPT) plan and an arc plan respectively.
Figure 17C:
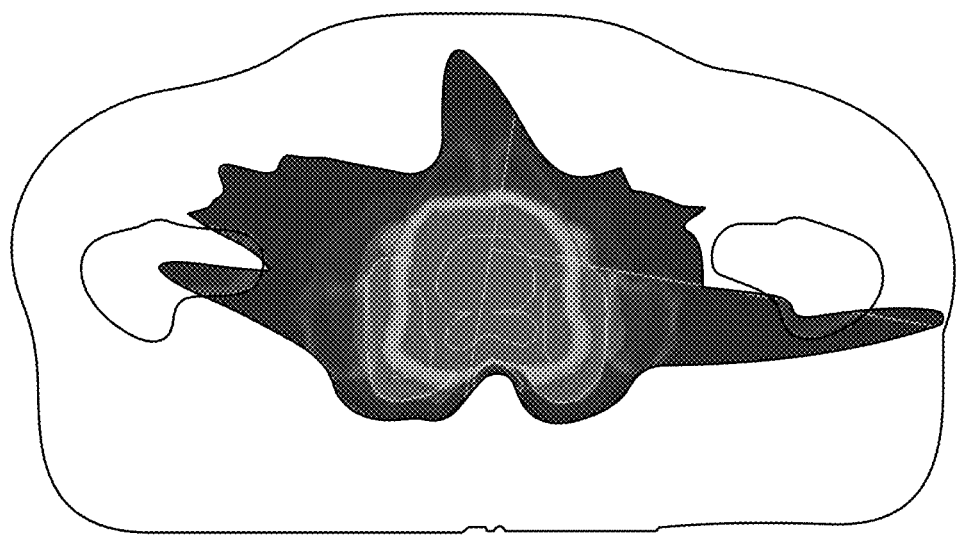

FIG. 17B and FIG. 17C show the 2D target dose distribution on the same slice of two fields IMPT plan and arc plan respectively. The arc plan utilizes more freedom of angles to distribute the desired target dose and thus can spare more dose to OARs like rectum and healthy tissues like left and right femurs.

Figure 18A:
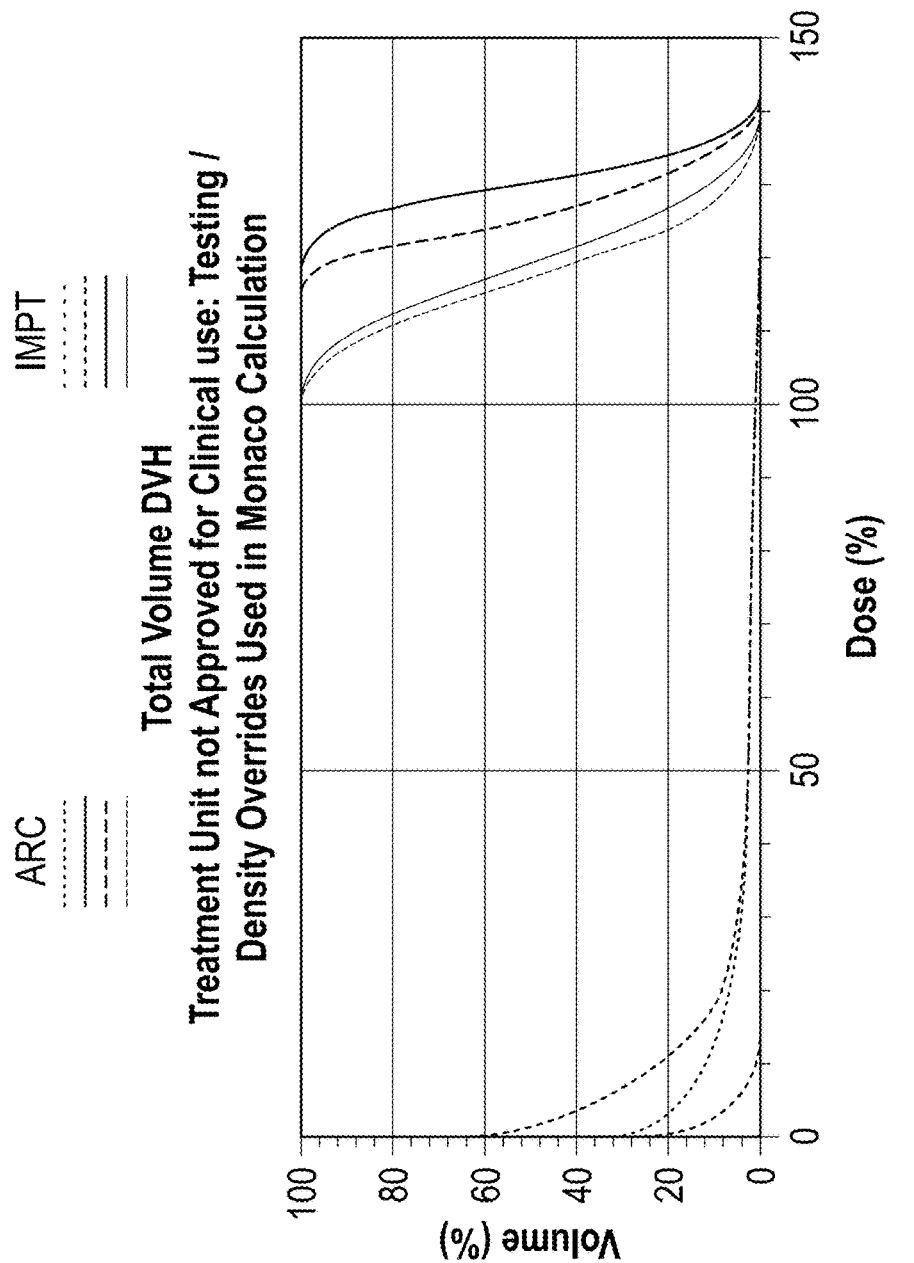
FIGS. 18A-18C illustrate proton arc planning compared to conventional four fields IMPT plan, in accordance with an embodiment.

FIG. 18A provides another example of proton arc planning compared to conventional four fields IMPT plan for brain metastases treatment. Similarly, DVH curves show a comparable target dosage while saving more dose delivered to the brain stem and even the whole brain. This is achieved by adopting a x % (here 55%) proximal target volume preference during the arc plan optimization. The aim of such planning preference is to spare dose to healthy tissue potentially delivered by spots passing through large parts of the brain.

Figure 18B:
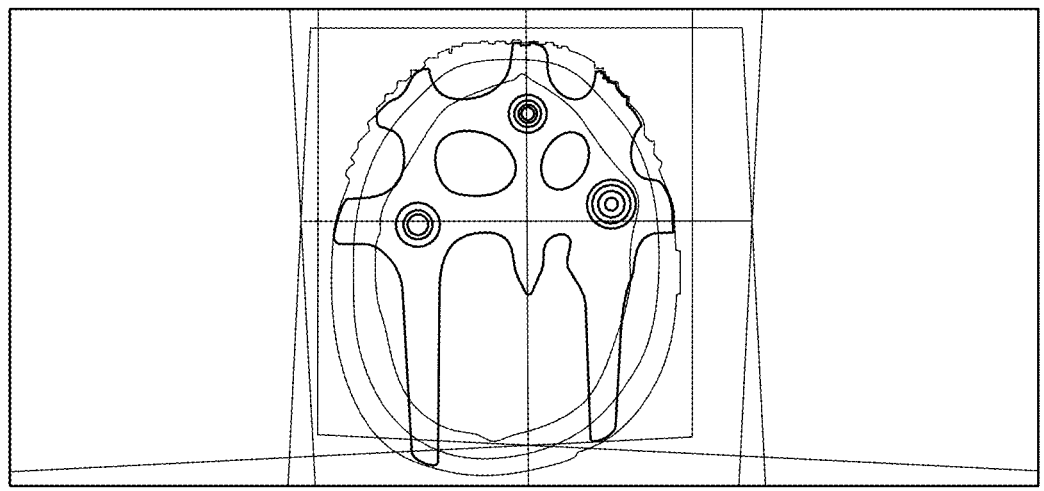
Figure 18C:
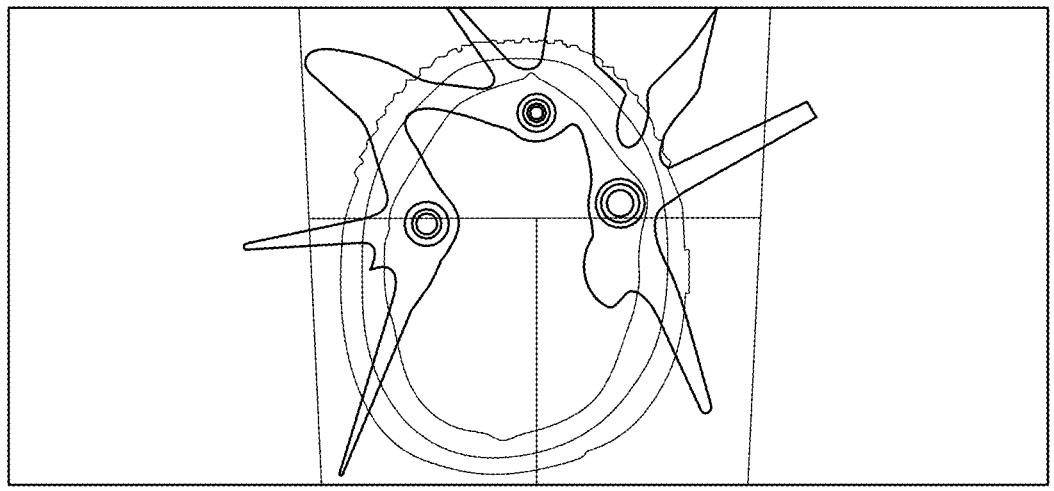

The 2D dose distribution of IMPT plan shown in FIG. 18B and the arc plan shown in FIG. 18C show obvious differences (e.g., advantage from OAR saving perspective) of the present systems and methods with a proper planning preference.

Figure 19:
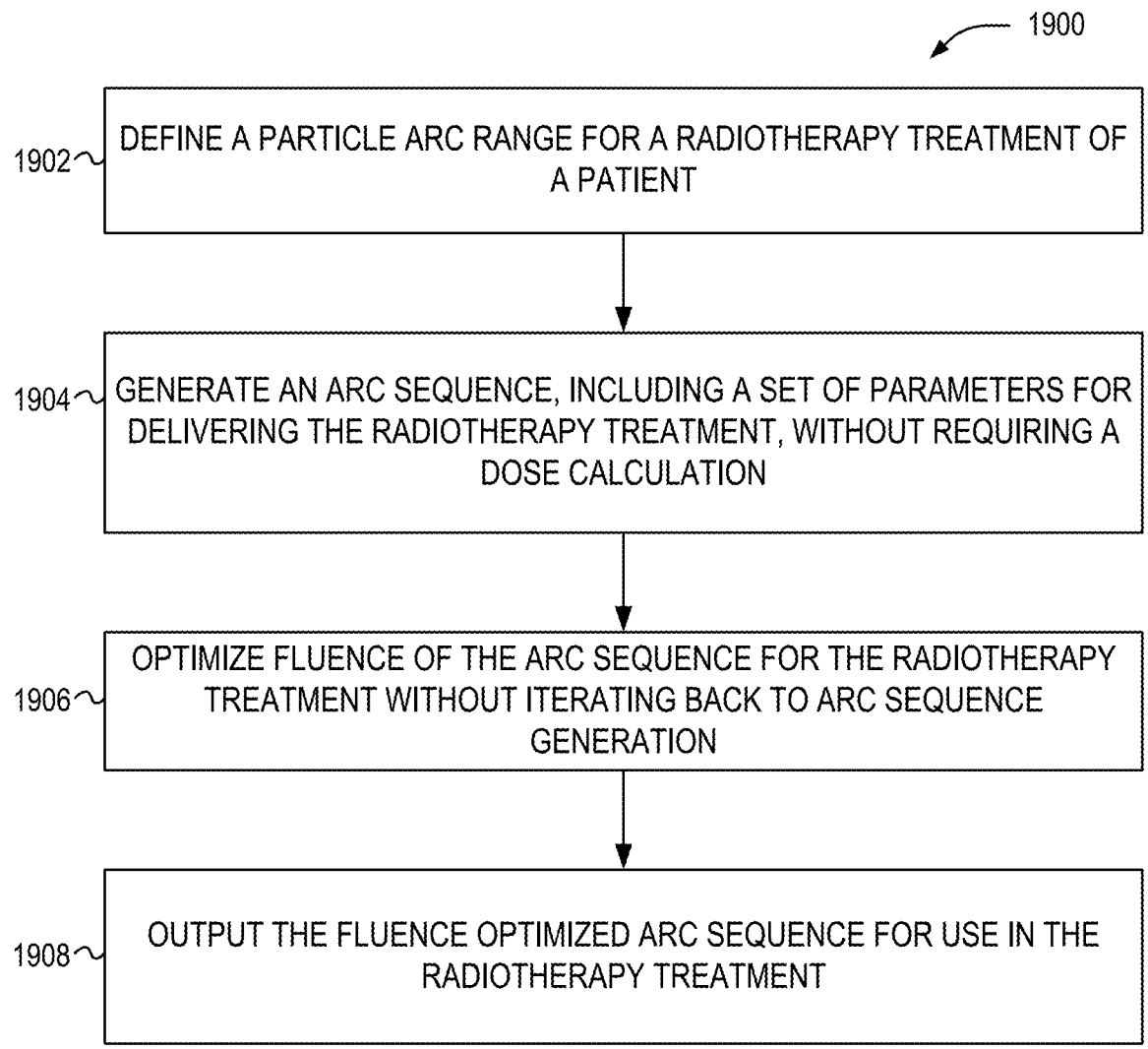
FIG. 19 illustrates a flowchart showing a technique for arc fluence optimization without iteration to arc sequence generation, in accordance with an embodiment.

FIG. 19 illustrates a flowchart showing a technique 1900 for arc fluence optimization without iteration to arc sequence generation, in accordance with an embodiment.

The technique 1900 includes an operation 1902 to define a particle arc range for a radiotherapy treatment of a patient. In an example, operation 1902 includes pre-optimization of the arc sequence or optimization of the arc sequence.

The technique 1900 includes an operation 1904 to generate an arc sequence, including a set of parameters for delivering the radiotherapy treatment, without requiring a dose calculation. In an example, operation 1904 includes wherein the set of parameters includes an organ at risk sparing level. In an example, a parameter of the set of parameters may include a high dose region per spot. The set of parameters may include an organ at risk region, such as covered by a specified number of paints. The set of parameters may include a predicted robustness of the arc sequence based on a plurality of errors that include at least one of patient geometry error, biological effects, delivery uncertainties, or device properties. In an example, the predicted robustness may be based on the patient geometry error, including lateral heterogeneity quantification for example.

In an example, the set of parameters of operation 1904 includes a target region covered by a specified number of paints. In this example, the target region may be represented by a high dose region. The high dose region may be delivered treatment such as by providing a very high dose radiation rate of at least 35-100 Gy/second. In this example, the target region may be represented by a high linear energy transfer (LET) region. In this example, the specified number of paints may include spots distributed over an entire solution space. The entire solution space may cover a particular angular distance. In this example, the target region may include additional uncertainty margins around a target tumor, wherein the uncertainty margins are at least one of a constant margin, a geometric margin, or an arc angle specific margin. The uncertainty margins may be angle specific margins that are range dependent beam direction margins and geometric lateral margins.

The set of parameters may include a predicted robustness of the arc sequence based on a plurality of errors that include patient geometry error, structure representation used for generating a spot sequence, or optimizing the fluence, at least one of which is based on a single image, multiple images, or a model. In an example, the patient geometry error and structure representation used for generating the spot sequence or optimizing the fluence are based on the multiple images, the multiple images including include images with intra- or inter-fraction changes.

The set of parameters may include a distribution complexity and an angular dependent target subregion selection. In an example, the set of parameters includes a target shape and an angular dependent target subregion selection. The set of parameters may include a predicted delivery efficiency based on hardware properties for delivering the radiotherapy treatment. In some examples, the set of parameters are used for optimizing delivery efficiency or optimizing for a desired delivery property.

In an example, the set of parameters may include a number of arcs or a number of arc segments. In this example, the set of parameters may include different parameters for different arcs among the number of arcs or different parameters for different arc segments among the number of arc segments.

In an example, the set of parameters may include parameters for robust optimization and plan evaluation during fluence optimization. In this example, the parameters for robust fluence optimization and plan evaluation may include errors in arc angle per spot or energy layer or arc segment or other patient geometry errors, biological effects, arc delivery uncertainties, or device properties.

In an example, generating the arc sequence includes providing a set of spots. In some examples, the set of spots is provided without requiring any use of a range shifting device or a range broadening device. In an example, the set of spots include a first subset of spots provided without requiring a range shifting or range broadening devices, and further include a second subset of spots provided requiring the use of a range shifting device or a range broadening device. In some examples, a set of spots may be provided with all spots using a range shifting device, a range broadening device, a blocking device, a lateral beam shape modifying device, or the like. The set of spots may be created based on specific settings including constant or dynamic spot placement.

Generating the arc sequence may include pre-optimization of the arc sequence. Pre-optimization may include using analytical methods, manually set methods, or artificial intelligence methods, such as before fluence optimization or as a preconfigured optimization.

The technique 1900 includes an operation 1906 to optimize fluence of the arc sequence for the radiotherapy treatment without iterating back to arc sequence generation. The arc sequence may include a set of potential optimum spots that further includes a particular minimum number of spots. The particular minimum number of spots may be generated by minimizing a number of redundant spots. Operation 1906 may include optimizing fluence of multiple arc sequences while maximizing damage to target tumor and minimizing damage to organs at risk.

In an example, optimizing the fluence of the arc sequence includes applying spot scanning optimization including robustness parameters, linear energy transfer (LET), biological parameters, hardware specific fluence properties, fluence smoothing methods, effects of previous treatments, simultaneous optimization of proton arc and other delivery types (photons, electrons, heavy ions and static proton beam methods), treatment type (SFUD, IMPT), or the like.

The technique 1900 includes an operation 1908 to output the fluence optimized arc sequence for use in the radiotherapy treatment. Operation 1908 may include outputting the fluence optimized arc sequence for display. Operation 1908 may include outputting the fluence optimized arc sequence to cause the radiotherapy treatment to occur. Operation 1908 may include saving the fluence optimized arc sequence for use in planning the radiotherapy treatment. In an example, the technique 1900 may include displaying, for example on a user interface, a visualization of a portion of the arc sequence including a trajectory and delivery parameters on a medical image or a model of anatomy of the patient.

The technique 1900 may include an operation to use a sequencer. The sequencer may be used to select spots in a high dose target region and spots in a high dose healthy tissue region, minimize (or reduce) a number of spots to the high dose healthy tissue region, and use the minimized (or reduced) number of spots for fluence optimization. In this example, optimizing fluence of the arc sequence may include minimizing a number of times a high dose is delivered to healthy tissue regions by changing weights of spots received from the sequencer, such that if one or more spots contribute to healthy tissue then their contribution is provided only once for a predetermined period of time. This example may include decreasing the weights assigned to the spots for any spot that provides a contribution to the high dose tissue region after the predetermined period of time is elapsed. This example may include further minimizing a contribution of spots outside the predetermined period of time. In an example, the predetermined period of time is approximately less than 500 milliseconds or approximately less than 100 milliseconds.

The technique 1900 may include an operation to perform robust evaluation for arc specific and arc non-specific robustness parameters as part of an arc plan review. The robustness parameters may include errors in delivery time, errors in arc angle, or errors in fluence per spot, energy layer, or arc segment.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

Example 1 is a method comprising: defining a particle arc range for a radiotherapy treatment of a patient; generating an arc sequence, including a set of parameters for delivering the radiotherapy treatment, without requiring a dose calculation; optimizing fluence of the arc sequence for the radiotherapy treatment without iterating back to arc sequence generation; and outputting the fluence optimized arc sequence for use in the radiotherapy treatment.

In Example 2, the subject matter of Example 1 includes, wherein the set of parameters includes a target region covered by a specified number of paints.

In Example 3, the subject matter of Example 2 includes, wherein the target region is represented by a high dose region.

In Example 4, the subject matter of Example 3 includes, wherein delivering treatment to the high dose region includes providing a very high dose radiation rate of at least 35-100 Gy/second.

In Example 5, the subject matter of Examples 2-4 includes, wherein the target region is represented by a high linear energy transfer (LET) region.

In Example 6, the subject matter of Examples 2-5 includes, wherein the specified number of paints include spots distributed over an entire solution space.

In Example 7, the subject matter of Example 6 includes, wherein the entire solution space covers a particular angular distance.

In Example 8, the subject matter of Examples 2-7 includes, wherein the target region includes additional uncertainty margins around a target tumor, wherein the uncertainty margins are at least one of a constant margin, a geometric margin, or an arc angle specific margin.

In Example 9, the subject matter of Example 8 includes, wherein the uncertainty margins are arc angle specific margins that are range dependent beam direction margins and geometric lateral margins.

In Example 10, the subject matter of Examples 1-9 includes, wherein a parameter of the set of parameters is a high dose region per spot.

In Example 11, the subject matter of Examples 1-10 includes, using a sequencer to: select spots in a high dose target region and spots in a high dose healthy tissue region; minimize a number of spots to the high dose healthy tissue region; and use the minimized number of spots for fluence optimization.

In Example 12, the subject matter of Example 11 includes, wherein optimizing fluence of the arc sequence includes minimizing a number of times a high dose is delivered to healthy tissue regions by changing weights of spots received from the sequencer, such that if one or more spots contribute to healthy tissue then their contribution is provided only once for a predetermined period of time.

In Example 13, the subject matter of Example 12 includes, wherein optimizing fluence of the arc sequence includes decreasing the weights assigned to the spots for any spot that provides a contribution to the high dose tissue region after the predetermined period of time is elapsed.

In Example 14, the subject matter of Example 13 includes, minimizing a contribution of spots outside the predetermined period of time.

In Example 15, the subject matter of Examples 12-14 includes, where the predetermined period of time is approximately less than 500 milliseconds.

In Example 16, the subject matter of Examples 12-15 includes, where the predetermined period of time is approximately less than 100 milliseconds.

In Example 17, the subject matter of Examples 1-16 includes, wherein the set of parameters includes a predicted robustness of the arc sequence based on a plurality of errors that include patient geometry error, structure representation used for generating a spot sequence, or optimizing the fluence, at least one of which is based on a single image, multiple images, or a model.

In Example 18, the subject matter of Example 17 includes, wherein the patient geometry error and structure representation used for generating the spot sequence or optimizing the fluence are based on the multiple images, the multiple images including include images with intra- or inter-fraction changes.

In Example 19, the subject matter of Examples 1-18 includes, wherein the arc sequence comprises a set of potential optimum spots that further includes a particular minimum number of spots.

In Example 20, the subject matter of Example 19 includes, wherein the particular minimum number of spots is generated by minimizing a number of redundant spots.

In Example 21, the subject matter of Examples 1-20 includes, wherein the generating the arc sequence includes pre-optimization of the arc sequence or optimization of the arc sequence.

In Example 22, the subject matter of Examples 1-21 includes, performing robust evaluation for arc specific and arc non-specific robustness parameters as part of an arc plan review.

In Example 23, the subject matter of Example 22 includes, wherein the robustness parameters include errors in delivery time, errors in arc angle, or errors in fluence per spot, energy layer, or arc segment.

In Example 24, the subject matter of Examples 1-23 includes, wherein generating the arc sequence includes providing a set of spots.

In Example 25, the subject matter of Example 24 includes, wherein the set of spots is provided without requiring any use of a range shifting device or a range broadening device.

In Example 26, the subject matter of Examples 24-25 includes, wherein the set of spots include a first subset of spots provided without requiring a range shifting or range broadening devices, and further include a second subset of spots provided requiring the use of a range shifting device or a range broadening device.

In Example 27, the subject matter of Examples 24-26 includes, wherein the set of spots is provided with all spots using a range shifting device or a range broadening device.

In Example 28, the subject matter of Examples 24-27 includes, wherein the set of spots is provided with all spots using blocking or lateral beam shape modifying devices.

In Example 29, the subject matter of Examples 24-28 includes, wherein the set of spots is created based on specific settings including constant or dynamic spot placement.

In Example 30, the subject matter of Examples 1-29 includes, wherein optimizing fluence of the arc sequence includes optimizing fluence of multiple arc sequences while maximizing damage to target tumor and minimizing damage to organs at risk.

Example 31 is a method comprising: defining a particle arc range for a radiotherapy treatment of a patient; generating an arc sequence, including a set of parameters for delivering the radiotherapy treatment, without requiring a dose calculation, wherein the set of parameters includes, an organ at risk sparing level; optimizing fluence of the arc sequence for the radiotherapy treatment without iterating back to arc sequence generation; and outputting the fluence optimized arc sequence for use in the radiotherapy treatment.

In Example 32, the subject matter of Example 31 includes, wherein the set of parameters includes an organ at risk region covered by a specified number of paints.

In Example 33, the subject matter of Examples 31-32 includes, wherein the set of parameters includes a predicted robustness of the arc sequence based on a plurality of errors that include at least one of patient geometry error, biological effects, delivery uncertainties, or device properties.

In Example 34, the subject matter of Example 33 includes, wherein the predicted robustness is based on the patient geometry error including lateral heterogeneity quantification.

In Example 35, the subject matter of Examples 31-34 includes, wherein the set of parameters includes a target shape and an angular dependent target subregion selection.

In Example 36, the subject matter of Examples 31-35 includes, wherein the set of parameters includes a distribution complexity and an angular dependent target subregion selection.

In Example 37, the subject matter of Examples 31-36 includes, wherein the set of parameters includes a predicted delivery efficiency based on hardware properties for delivering the radiotherapy treatment.

In Example 38, the subject matter of Examples 31-37 includes, wherein the set of parameters are used for optimizing delivery efficiency or optimizing for a desired delivery property.

In Example 39, the subject matter of Examples 31-38 includes, wherein the set of parameters includes a number of arcs or a number of arc segments.

In Example 40, the subject matter of Example 39 includes, wherein the set of parameters include different parameters for different arcs among the number of arcs or different parameters for different arc segments among the number of arc segments.

In Example 41, the subject matter of Examples 31-40 includes, wherein the set of parameters further includes parameters for robust optimization and plan evaluation during fluence optimization.

In Example 42, the subject matter of Example 41 includes, wherein the parameters for robust fluence optimization and plan evaluation include errors in arc angle per spot or energy layer or arc segment or other patient geometry errors, biological effects, arc delivery uncertainties, or device properties.

In Example 43, the subject matter of Examples 31-42 includes, wherein generating the arc sequence includes pre-optimization of the arc sequence.

In Example 44, the subject matter of Example 43 includes, wherein the pre-optimization includes using analytical methods, manually set methods, or artificial intelligence methods.

In Example 45, the subject matter of Examples 31-44 includes, wherein optimizing the fluence of the arc sequence includes applying spot scanning optimization including robustness parameters, linear energy transfer (LET), biological parameters, hardware specific fluence properties, fluence smoothing methods, and effects of previous treatments.

In Example 46, the subject matter of Examples 31-45 includes, displaying, on a user interface, a visualization of a portion of the arc sequence including a trajectory and delivery parameters on a medical image or a model of anatomy of the patient.

Example 47 is at least one machine-readable medium including instructions that, when executed by processing circuitry, cause the processing circuitry to perform operations to implement of any of Examples 1-46.

Example 48 is an apparatus comprising means to implement of any of Examples 1-46.

Example 49 is a system to implement of any of Examples 1-46.

What is claimed is:

1. A method comprising:
   defining a particle arc range for a radiotherapy treatment of a patient;
   generating an arc sequence, including a set of parameters for delivering the radiotherapy treatment, without requiring a dose calculation;
   optimizing fluence of the arc sequence for the radiotherapy treatment without iterating back to arc sequence generation and without modifying the generated arc sequence; and
   outputting the fluence optimized arc sequence for use in the radiotherapy treatment.

2. The method of claim 1, wherein the set of parameters includes a target region covered by a specified number of paints.

3. The method of claim 2, wherein the target region is represented by a Bragg peak target dose region.

4. The method of claim 3, wherein delivering treatment to the Bragg peak target dose region includes providing a dose radiation rate of at least 35-100 Gy/second.

5. The method of claim 2, wherein the target region is represented by a maximum linear energy transfer (LET) region among treatment regions.

6. The method of claim 2, wherein the specified number of paints includes spots distributed over an entire solution space.

7. The method of claim 6, wherein the entire solution space covers a particular angular distance.

8. The method of claim 2, wherein the target region includes additional uncertainty margins around a target tumor, wherein the uncertainty margins are at least one of a constant margin, a geometric margin, or an arc angle specific margin.

9. The method of claim 8, wherein the uncertainty margins are arc angle specific margins that are range dependent beam direction margins and geometric lateral margins.

10. The method of claim 1, wherein a parameter of the set of parameters includes a location of a Bragg peak region of each spot.

11. The method of claim 1, further comprising using a sequencer to:
    select spots in a Bragg peak target dose target region and spots in a Bragg peak target dose healthy tissue region;
    minimize a number of spots to the Bragg peak target dose healthy tissue region; and
    use the minimized number of spots for fluence optimization.

12. The method of claim 11, wherein optimizing fluence of the arc sequence includes minimizing a number of times a Bragg peak target dose is delivered to healthy tissue regions by changing weights of spots received from the sequencer, such that if one or more spots contribute to healthy tissue then their contribution is provided only once for a predetermined period of time.

13. The method of claim 12, wherein optimizing fluence of the arc sequence includes decreasing a weight of any spot that provides a contribution to the Bragg peak target dose tissue region after the predetermined period of time is elapsed.

14. The method of claim 13, further comprising minimizing a contribution of spots outside the predetermined period of time.

15. The method of claim 12, where the predetermined period of time is approximately less than 500 milliseconds.

16. The method of claim 12, where the predetermined period of time is approximately less than 100 milliseconds.

17. The method of claim 1, wherein the set of parameters includes a predicted robustness of the arc sequence based on a plurality of errors that include patient geometry error, structure representation used for generating a spot sequence, or optimizing the fluence, at least one of which is based on a single image, multiple images, or a model.

18. The method of claim 17, wherein the patient geometry error and structure representation used for generating the spot sequence or optimizing the fluence are based on the multiple images, the multiple images including include images with intra- or inter-fraction changes.

19. The method of claim 1, wherein the arc sequence comprises a set of potential optimum spots that further includes a particular minimum number of spots.

20. The method of claim 19, wherein the particular minimum number of spots is generated by minimizing a number of redundant spots.

21. The method of claim 1, wherein the generating the arc sequence includes pre-optimization of the arc sequence or optimization of the arc sequence.

22. The method of claim 1, further comprising performing robust evaluation for arc specific and arc non-specific robustness parameters as part of an arc plan review.

23. The method of claim 22, wherein the robustness parameters include errors in delivery time, errors in arc angle, or errors in fluence per spot, energy layer, or arc segment.

24. The method of claim 1, wherein generating the arc sequence includes providing a set of spots.

25. The method of claim 24, wherein the set of spots is provided without requiring any use of a range shifting device or a range broadening device.

26. The method of claim 24, wherein the set of spots includes a first subset of spots provided without requiring a range shifting or range broadening device, and further includes a second subset of spots provided requiring the use of a range shifting device or a range broadening device.

27. The method of claim 24, wherein the set of spots is provided with all spots using a range shifting device or a range broadening device.

28. The method of claim 24, wherein the set of spots is provided with all spots using blocking or lateral beam shape modifying devices.

29. The method of claim 24, wherein the set of spots is created based on specific settings including constant or dynamic spot placement.

30. The method of claim 1, wherein optimizing fluence of the arc sequence includes optimizing fluence of multiple arc sequences while maximizing damage to a target tumor and minimizing damage to organs at risk.

\* \* \* \* \*